(12) United States Patent
Failli et al.

(10) Patent No.: US 6,903,091 B2
(45) Date of Patent: Jun. 7, 2005

(54) BIPHENYL VASOPRESSIN AGONISTS

(75) Inventors: Amedeo A. Failli, Princeton Junction, NJ (US); Thomas J. Caggiano, Morrisville, PA (US); Jay S. Shumsky, Hightstown, NJ (US); Eugene J. Trybulski, Princeton Junction, NJ (US); Kevin A. Memoli, Cranbury, NJ (US); John P. Dusza, Nanuet, NY (US)

(73) Assignee: Wyeth, Madison, NJ (US)

( * ) Notice: Subject to any disclaimer, the term of this patent is extended or adjusted under 35 U.S.C. 154(b) by 13 days.

(21) Appl. No.: 10/121,156

(22) Filed: Apr. 11, 2002

(65) Prior Publication Data

US 2003/0018024 A1 Jan. 23, 2003

Related U.S. Application Data

(60) Provisional application No. 60/283,263, filed on Apr. 12, 2001.

(51) Int. Cl.[7] ............... C07D 471/04; C07D 487/04; C07D 401/06; A61K 31/55; A61P 3/10
(52) U.S. Cl. ........... 514/220; 540/561; 540/557; 540/553; 540/593; 540/558
(58) Field of Search ................ 540/561; 514/220

(56) References Cited

U.S. PATENT DOCUMENTS

| | | | |
|---|---|---|---|
| 5,516,774 A | | 5/1996 | Albright |
| 5,521,173 A | * | 5/1996 | Venkatesan et al. ........ 514/220 |
| 5,532,235 A | | 7/1996 | Albright |
| 5,536,718 A | | 7/1996 | Albright |
| 5,610,156 A | | 3/1997 | Albright |
| 5,612,334 A | | 3/1997 | Albright |
| 5,624,923 A | | 4/1997 | Albright |
| 5,654,297 A | | 8/1997 | Albright |
| 5,686,445 A | | 11/1997 | Albright |
| 5,693,635 A | | 12/1997 | Albright |
| 5,696,112 A | | 12/1997 | Albright |
| 5,700,796 A | | 12/1997 | Albright |
| 5,719,278 A | | 2/1998 | Albright |
| 5,733,905 A | | 3/1998 | Albright |
| 5,736,538 A | | 4/1998 | Albright |
| 5,736,540 A | | 4/1998 | Albright |
| 5,739,128 A | | 4/1998 | Albright |
| 5,747,487 A | | 5/1998 | Albright |
| 5,753,648 A | | 5/1998 | Albright et al. |
| 5,760,031 A | | 6/1998 | Albright |
| 5,780,471 A | | 7/1998 | Venkatesan |
| 5,849,735 A | | 12/1998 | Albright |
| 6,096,736 A | | 8/2000 | Ogawa et al. |

FOREIGN PATENT DOCUMENTS

| | | |
|---|---|---|
| WO | WO 9534540 | 12/1995 |
| WO | WO 9622282 | 7/1996 |
| WO | WO 9722591 | 6/1997 |
| WO | WO 9965525 | 12/1999 |
| WO | WO 0043398 | 7/2000 |

OTHER PUBLICATIONS

Beitz and Schultz, Current Medicinal Chemistry, 1999, 457–467, 6.

Goodman and Gilman, The Pharmacological Basis of Therapeutics, 1996, 715–731, 9th Edition.

Lethagen, Ann. Hematol., 1994, 173–180, 69.

Cash et al., Brit. J. Haematol., 1974, 363–364, 27.

David, Regulatory Peptides, 1993, 311–317, 45.

Burggraaf et al., Cli. Sci., 1994, 497–503, 86.

* cited by examiner

*Primary Examiner*—Mark L. Berch
*Assistant Examiner*—Kahsay Habte
(74) *Attorney, Agent, or Firm*—Michael P. Straher; Cozen O'Connor

(57) ABSTRACT

A compound of the formulae (I) or (II):

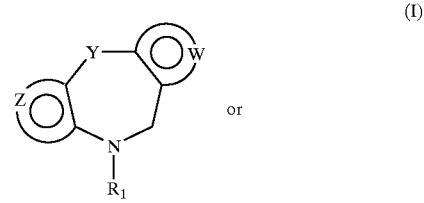

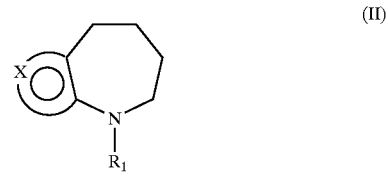

wherein:

Y is a moiety selected from NR or —$(CH_2)_n$—;
wherein R is hydrogen or ($C_1$–$C_6$) lower alkyl, and n is 1;

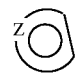

represents:

(1) a phenyl ring optionally substituted with one or two substituents selected, independently, from the group comprising hydrogen, ($C_1$–$C_6$) lower alkyl, halogen, cyano, $CF_3$, hydroxy, ($C_1$–$C_6$) lower alkoxy, ($C_1$–$C_6$) lower alkoxy carbonyl, carboxy, —$CONH_2$, —CONH [($C_1$–$C_6$) lower alkyl], —CON[($C_1$–$C_6$) lower alkyl]$_2$; or (2) a 6-membered aromatic (unsaturated) heterocyclic ring having one nitrogen atom, optionally substituted by ($C_1$–$C_6$) lower alkyl, halogen or ($C_1$–$C_6$) lower alkoxy;

represents:

(1) a phenyl ring optionally substituted with one or two substituents selected, independently, from the group comprising hydrogen, ($C_1$–$C_6$) lower alkyl, halogen, cyano, $CF_3$, hydroxy, ($C_1$–$C_6$) lower alkoxy, or ($C_1$–$C_6$) lower alkoxy carbonyl, carboxy, —$CONH_2$, —CONH[($C_1$–$C_6$) lower alkyl], —CON[($C_1$–$C_6$) lower alkyl]$_2$; or (2) a 5-membered aromatic (unsaturated) heterocyclic ring having one nitrogen atom, optionally substituted by ($C_1$–$C_6$) lower alkyl, ($C_1$–$C_6$) lower alkoxy, or halogen; or (3) a 6-membered aromatic (unsaturated) heterocyclic ring having one nitrogen atom, optionally substituted by ($C_1$–$C_6$) lower alkyl, halogen, or ($C_1$–$C_6$) lower alkoxy;

represents a 5-membered aromatic (unsaturated) heterocyclic ring having one sulfur atom, optionally substituted by ($C_1$–$C_6$) lower alkyl, halogen, or ($C_1$–$C_6$) lower alkoxy;

$R_1$ is a moiety of the formula

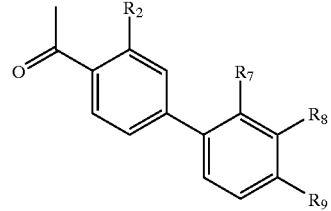

or

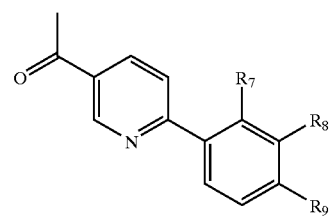

and $R_2$, $R_3$, $R_7$, $R_8$ and $R_9$ are, independently, selected from a group consisting of hydrogen, ($C_1$–$C_3$) lower alkyl, $OCH_3$, halogen, $CF_3$, —$SCH_3$, $OCF_3$, $SCF_3$, or CN;

or a pharmaceutically acceptable salt, or pro-drug form thereof.

6 Claims, No Drawings

BIPHENYL VASOPRESSIN AGONISTS

This application claims the benefit of U.S. application Ser. No. 60/283,263, filed on Apr. 12, 2001.

This invention concerns biphenyls which act as vasopressin $V_2$ agonists, as well as methods of treatment and pharmaceutical compositions utilizing these compounds.

BACKGROUND OF THE INVENTION

Vasopressin plays a vital role in the conservation of water by concentrating the urine in the collecting ducts of the kidney. The collecting ducts of the kidney are relatively impermeable to water without the presence of vasopressin at the receptors and therefore, the hypotonic fluid formed after filtering through the glomeruli, passing the proximal convoluted tubule, the loops of Henle, and the distal convoluted tubules, will be excreted as dilute urine. However, during dehydration, volume depletion or blood loss, vasopressin is released from the brain and activates the vasopressin $V_2$ receptors in the collecting ducts of the kidney rendering the ducts very permeable to water; hence water is reabsorbed and a concentrated urine is excreted. Aquaporins (water channel membrane proteins) play a major role in this intricate process (for a review on mammalian aquaporins, see Beitz and Schultz, *Current Medicinal Chemistry*, 6, 457–467 (1999)). In patients and animals with central or neurogenic diabetes insipidus, the synthesis of vasopressin in the brain is defective and therefore, they produce very little or no vasopressin, but their vasopressin receptors in the kidneys are normal. Because they cannot concentrate the urine, they may produce as much as 10 times the urine volumes of their healthy counterparts and are very sensitive to the action of vasopressin and vasopressin $V_2$ agonists. Vasopressin and desmopressin, (1-desamino-8D-arginine vasopressin) which is a peptide analog of the natural vasopressin, are being used in patients with central diabetes insipidus. Vasopressin $V_2$ agonists are also useful for the treatment of nocturnal enuresis, nocturia, urinary incontinence and temporary delay of urination, whenever desirable.

Vasopressin, through activation of its $V_{1a}$ receptors, exerts vasoconstricting effects so as to raise blood pressure. A vasopressin $V_{1a}$ receptor antagonist will counteract this effect. Vasopressin and vasopressin-like agonists cause release factor VIII and von Willebrand factor from intracellular stores, so they are useful for the treatment of bleeding disorders, such as hemophilia. Vasopressin and vasopressin-like agonists also release tissue-type plasminogen activator (t-PA) into the blood circulation so they are useful in dissolving blood clots such as in patients with myocardial infarction and other thromboembolic disorders (Jackson, "Vasopressin and other agents affecting the renal conservation of water", in Goodman and Gilman, *The Pharmacological Basis of Therapeutics*, 9th ed., Hadman, Limbird, Molinoff, Ruddon and Gilman Eds., McGraw-Hill, New York, pp. 715–731 (1996); Lethagen, *Ann. Hematol.* 69, 173–180 (1994); Cash et al., *Brit. J. Haematol.*, 27, 363–364 (1974); David, *Regulatory Peptides*, 45, 311–317 (1993); Burggraaf et al., *Cli. Sci.*, 86, 497–503 (1994)).

Non-peptidic vasopressin antagonists have recently been disclosed. Albright et al. describe tricyclic azepines as vasopressin antagonists or vasopressin and oxytocin antagonists in U.S. Pat. No. 5,516,774 (1996), U.S. Pat. No. 5,532,235 (1996), U.S. Pat. Nos. 5,536,718, 5,610,156 (1997), U.S. Pat. No. 5,612,334 (1997), U.S. Pat. No. 5,624,923 (1997), U.S. Pat. No. 5,654,297 (1997), U.S. Pat. No. 5,686,445 (1997), U.S. Pat. No. 5,693,635 (1997), U.S. Pat. No. 5,696,112 (1997), U.S. Pat. No. 5,700,796 (1997), U.S. Pat. No. 5,719,278 (1998), U.S. Pat. No. 5,733,905 (1998), U.S. Pat. No. 5,736,538 (1998), U.S. Pat. No. 5,736,540 (1998), U.S. Pat. No. 5,739,128 (1998), U.S. Pat. No. 5,747,487 (1998), U.S. Pat. No. 5,753,648 (1998), U.S. Pat. No. 5,760,031 (1998), U.S. Pat. No. 5,780,471 (1998); tetrahydrobenzodiazepine derivatives as vasopressin antagonists are disclosed in J.P. 0801460-A (1996); Ogawa et al., disclose benzoheterocyclic derivatives as vasopressin and oxytocin antagonists, and as vasopressin agonists in WO 9534540-A; Ogawa et al. disclose benzazepine derivatives with anti-vasopressin activity, oxytocin antagonistic activity and vasopressin agonist activity, useful as vasopressin antagonists, vasopressin agonists and oxytocin antagonists in WO 97/22951 (1997) and U.S. Pat. No. 6,096,736 (2000); and Venkatesan et al., disclose tricyclic benzazepine derivatives as vasopressin and oxytocin antagonists in U.S. Pat. No. 5,521,173 (1996). Ohtahe et al. disclose ocular tension lowering agents and phosphoric ester derivatives exhibiting vasopressin $V_1$ receptor antagonism in WO 99/65525 (1999); and Hoekstra et al. disclose tricyclic benzodiazepines useful as vasopressin receptor antagonists for treating conditions involving increased vascular resistance and cardiac insufficiency in WO 00/43398 (2000).

Albright et al., disclose a subset of tricyclic dibenzodiazepines, pyrrolo benzodiazepines and pyrrolo pyridodiazepines related to the present application, as $V_1$ and/or $V_2$ vasopressin receptor antagonists and oxytocin receptor antagonists in U.S. Pat. No. 5,849,735 (1998) and WO 96/22282 A1 (1996), inter alia.

Albright et al., disclose a subset of tricyclic benzazepines as $V_1$ and/or $V_2$ vasopressin receptor antagonists and oxytocin receptor antagonists in U.S. Pat. No. 5,532,235 (1996).

Venkatesan et al. also teach a subset of tricyclic benzazepines with vasopressin and oxytocin antagonist activity in U.S. Pat. No. 5,521,173 (1996), WO 96/22292 (1996), and U.S. Pat. No. 5,780,471 (1998).

Albright et al., also broadly describe a subset of bicyclic azepines as $V_1$ and/or $V_2$ vasopressin receptor antagonists and oxytocin receptor antagonists in U.S. Pat. No. 5,696,112 (1997), and WO 96/22294.

SUMMARY OF THE INVENTION

This invention relates to novel and known compounds selected from those of formula (I) or (II):

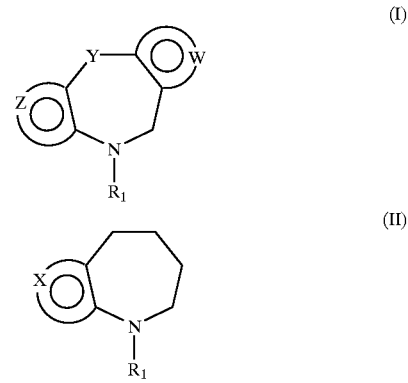

wherein:
Y is a moiety selected from NR or —$(CH_2)_n$—;
wherein R is hydrogen or ($C_1$–$C_6$) lower alkyl,
and n is 1;

represents (1) a phenyl ring optionally substituted with one or two substituents selected, independently, from the group comprising hydrogen, $(C_1-C_6)$ lower alkyl, halogen, cyano, $CF_3$, hydroxy, $(C_1-C_6)$ lower alkoxy, $(C_1-C_6)$ lower alkoxy carbonyl, carboxy, —$CONH_2$, —$CONH[(C_1-C_6)$ lower alkyl], —$CON[(C_1-C_6)$ lower alkyl]$_2$; or (2) a 6-membered aromatic (unsaturated) heterocyclic ring having one nitrogen atom, optionally substituted by $(C_1-C_6)$ lower alkyl, halogen or $(C_1-C_6)$ lower alkoxy;

represents (1) a a phenyl ring optionally substituted with one or two substituents selected, independently, from the group comprising hydrogen, $(C_1-C_6)$ lower alkyl, halogen, cyano, $CF_3$, hydroxy, $(C_1-C_6)$ lower alkoxy, or $(C_1-C_6)$ lower alkoxy carbonyl, carboxy, —$CONH_2$, —$CONH[(C_1-C_6)$ lower alkyl], —$CON[(C_1-C_6)$ lower alkyl]$_2$;

or (2) a 5-membered aromatic (unsaturated) heterocyclic ring having one nitrogen atom, optionally substituted by $(C_1-C_6)$ lower alkyl, $(C_1-C_6,)$ lower alkoxy, or halogen;

or (3) a 6-membered aromatic (unsaturated) heterocyclic ring having one nitrogen atom, optionally substituted by $(C_1-C_6)$ lower alkyl, halogen, or $(C_1-C_6)$ lower alkoxy;

represents a 5-membered aromatic (unsaturated) heterocyclic ring having one sulfur atom, optionally substituted by $(C_1-C_6)$ lower alkyl, halogen, or $(C_1-C_6)$ lower alkoxy;

$R_1$ is a moiety of the formula

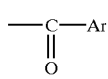

wherein Ar is a moiety:

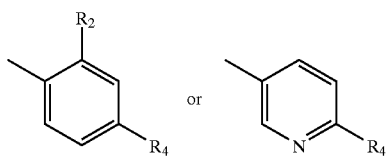

$R_4$ is the moiety

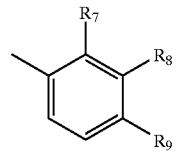

and $R_2$, $R_7$, $R_8$ and $R_9$ are, independently, selected from a group consisting of hydrogen, $(C_1-C_3)$ lower alkyl, $OCH_3$, halogen, $CF_3$, $SCH_3$, $OCF_3$, $SCF_3$, or CN;

or a pharmaceutically acceptable salt, or pro-drug form thereof.

One subset of compounds of this invention comprises those of the formulae:

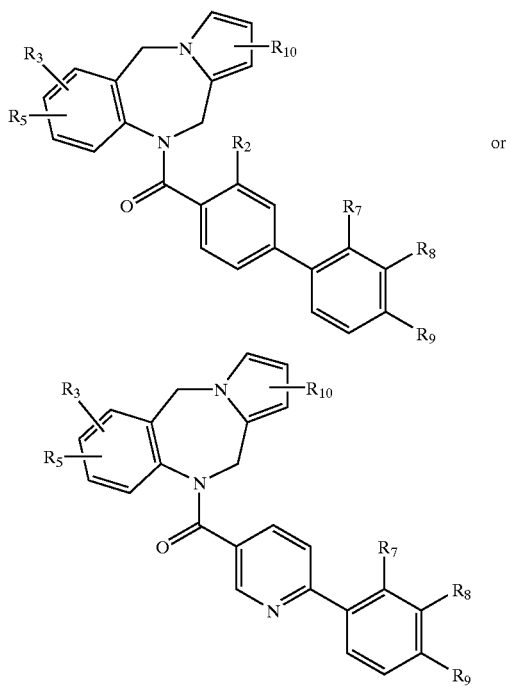

wherein:

$R_3$ and $R_5$ are independently selected from H, $C_1-C_6$ alkyl, halogen, cyano, $CF_3$, hydroxy, $C_1-C_6$ alkoxy, $C_1-C_6$ alkoxy carbonyl, carboxy, —$CONH_2$, —CONH [$C_1-C_6$ alkyl], —$CON[C_1-C_6$ alkyl]$_2$;

$R_2$, $R_7$, $R_8$ and $R_9$ are each, independently, selected from the group of hydrogen, $C_1-C_3$ alkyl, $OCH_3$, halogen, $CF_3$, $SCH_3$, $OCF_3$, $SCF_3$, or CN; and $R_{10}$ is a group selected from $C_1-C_6$ alkyl, halogen, or $C_1-C_6$ alkoxy; or a pharmaceutically acceptable salt or prodrug form thereof.

Another group of compounds of this invention comprises those of the formulae:

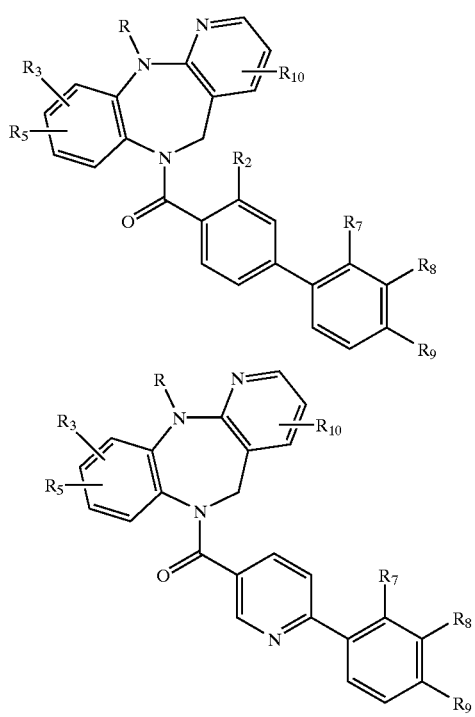

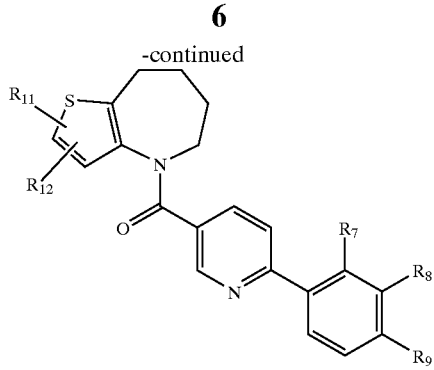

wherein:

$R_2$, $R_7$, $R_8$ and $R_9$ are each, independently, selected from the group of hydrogen, $C_1$–$C_3$ alkyl, $OCH_3$, halogen, $CF_3$, $SCH_3$, $OCF_3$, $SCF_3$, or CN; and $R_{11}$ and $R_{12}$ are independently selected from $C_1$–$C_6$ alkyl, halogen, or $C_1$–$C_6$ alkoxy;

or a pharmaceutically acceptable salt or prodrug form thereof.

A further group of compounds of this invention comprises those of the formulae:

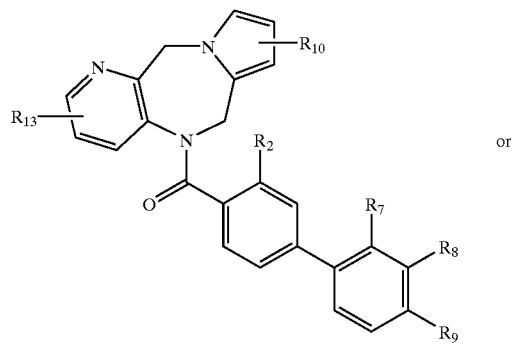

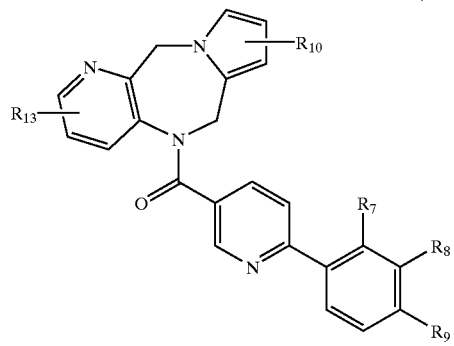

wherein:

R is hydrogen or $C_1$–$C_6$ alkyl;

$R_3$ and $R_5$ are independently selected from H, $C_1$–$C_6$ alkyl, halogen, cyano, $CF_3$, hydroxy, $C_1$–$C_6$ alkoxy, $C_1$–$C_6$ alkoxy carbonyl, carboxy, —$CONH_2$, —CONH[$C_1$–$C_6$ alkyl], —CON[$C_1$–$C_6$ alkyl]$_2$;

$R_2$, $R_7$, $R_8$ and $R_9$ are each, independently, selected from the group of hydrogen, $C_1$–$C_3$ alkyl, $OCH_3$, halogen, $CF_3$, $SCH_3$, $OCF_3$, $SCF_3$, or CN; and $R_{10}$ is a group selected from $C_1$–$C_6$ alkyl, halogen, or $C_1$–$C_6$ alkoxy;

or a pharmaceutically acceptable salt or prodrug form thereof.

Another group of compounds of this invention comprise those of the formulae:

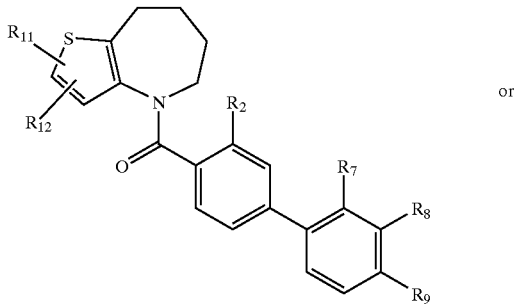

wherein $R_2$, $R_7$, $R_8$, and $R_9$ are each, independently, selected from the group of hydrogen, $C_1$–$C_3$ alkyl, $OCH_3$, halogen, $CF_3SCH_3$, $OCF_3$, $SCF_3$, or CN;

$R_{10}$ is a group selected from $C_1$–$C_6$ alkyl, halogen, or $C_1$–$C_6$ alkoxy; and $R_{13}$ is $C_1$–$C_6$ alkyl, halogen or $C_1$–$C_6$ alkoxy;

or a pharmaceutically acceptable salt or prodrug form thereof.

A separate subgroup of compounds of this invention comprises those of the formulae:

wherein:

R is hydrogen or $C_1$–$C_6$ alkyl;

$R_3$, $R_5$, $R_{3'}$, and $R_{5'}$, are independently selected from H, $C_1$–$C_6$ alkyl, halogen cyano, $CF_3$, hydroxy, $C_1$–$C_6$ alkoxy, $C_1$–$C_6$ alkoxy carbonyl, carboxy, —$CONH_2$, —CONH[$C_1$–$C_6$ alkyl], —CON[$C_1$–$C_6$ alkyl]$_2$;

$R_2$, $R_7$, $R_8$ and $R_9$ are each, independently, selected from the group of hydrogen, $C_1$–$C_3$ alkyl, $OCH_3$, halogen, $CF_3$, $SCH_3$, $OCF_3$, $SCF_3$, or CN; and or a pharmaceutically acceptable salt or prodrug form thereof.

As used herein the term "lower", as used in relation to alkoxy or alkyl, is understood to refer to those groups having from 1 to 6 carbon atoms. Halogen refers to fluorine, chlorine, bromine or iodine.

Among the preferred compounds of this invention are:

EXAMPLE 1
(2'-Methoxy-[1,1'-biphenyl]-4-yl)-(5H,11H-pyrrolo[2,1-c][1,4]benzodiazepin-10-yl)-methanone

EXAMPLE 2
(10,11-Dihydro-5H-pyrrolo[2,1-c][1,4]benzodiazepin-10-yl)-(3'-methyl-[1,1'-biphenyl]-4-yl)-methanone

EXAMPLE 3
(10,11-Dihydro-5H-pyrrolo[2,1-c][1,4]benzodiazepin-10-yl)-(4'-methoxy-[1,1'-biphenyl]-4-yl)-methanone;

EXAMPLE 4
[1,1'-Biphenyl]-4-yl-(5,11-dihydro-benzo[b]pyrido[2,3-e][1,4]diazepin-6-yl)-methanone;

EXAMPLE 5
[1,1'-Biphenyl]-4-yl-(11-methyl-5,11-dihydro-benzo[b]pyrido[2,3-e][1,4]diazepin-6-yl)-methanone;

EXAMPLE 6
[1,1'-Biphenyl]-4-yl-(5,11-dihydro-10H-dibenzo[b,e][1,4]diazepin-10-yl)methanone;

EXAMPLE 7
[1,1'-Biphenyl]-4-yl-(5-methyl-5,11-dihydro-10H-dibenzo[b,e][1,4]diazepin-10-yl)methanone;

EXAMPLE 8
[1,1'-Biphenyl]-4-yl-(5,6,7,8-tetrahydro-thieno[3,2-b]azepin-4-yl)-methanone;

EXAMPLE 9
(5H,11H-Benzo[e]pyrrolo[1,2-a][1,4]diazepin-10-yl)-(6-phenyl-pyridin-3-yl)-methanone;

EXAMPLE 10
(5H,11H-Benzo[e]pyrrolo[1,2-a][1,4]diazepin-10-yl)-(4'-methoxy-3-methyl-[1,1'-biphenyl]-4-yl)-methanone;

EXAMPLE 11
[1,1'-Biphenyl]-4-yl-(4H, 10H-3a,5,9-triaza-benzo[f]azulen-9-yl)-methanone;

It is understood by those practicing the art that some of the compounds of this invention may contain one or more asymmetric centers and may thus give rise to stereoisomers and diastereomers. The present invention includes such stereoisomers and diastereomers; as well as the racemic and resolved, enantiomerically pure stereoisomers and pharmaceutically acceptable salts thereof, which possess the indicated activity. Stereoisomers may be obtained in pure form by standard procedures known to those skilled in the art. It is also understood that this invention encompasses all possible regioisomers, and mixtures thereof which possess the indicated activity. Such regioisomers may be obtained in pure form by standard separation procedures known to those skilled in the art.

Also according to the present invention there is provided a method of treating disorders which are remedied or alleviated by vasopressin receptor agonist activity including, but not limited to, diabetes insipidus, nocturnal enuresis, nocturia, urinary incontinence, or bleeding and coagulation disorders. This invention also provides a method of inducing temporary delay of urination whenever desirable in humans or other mammals. Each of these methods comprises administering to a human or other mammal in need thereof an effective amount of a compound or a pharmaceutical composition of the invention.

The present invention accordingly provides a pharmaceutical composition which comprises a pharmaceutically effective amount of a compound of this invention in combination or association with a pharmaceutically acceptable carrier or excipient. In particular, the present invention provides a pharmaceutical composition which comprises an effective amount of a compound of this invention and a pharmaceutically acceptable carrier. A pharmaceutically effective amount of a compound herein is understood to be at least the minimum amount which will provide a desirable result in inducing a temporary delay in urination or in remedying, inhibiting or alleviating the malady in question or providing relief from its symptoms.

The compositions are preferably adapted for oral administration. However, they may be adapted for other modes of administration, for example, parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 1000 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

Also according to the present invention there are provided processes for producing the compounds of the present invention.

PROCESS OF THE INVENTION

The compounds of the present invention of general formula (I) may be conveniently prepared according to the process shown in Scheme I.

Scheme I

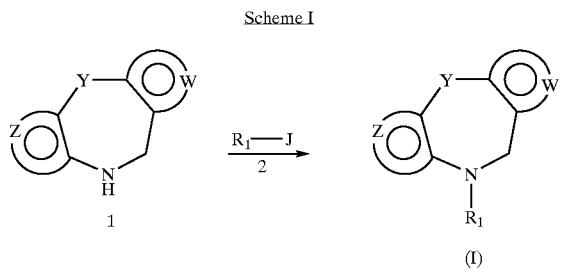

(I)

Thus, a tricyclic azepine (diazepine) of formula (1) is treated with an appropriately substituted acylating agent such as an aroyl halide, preferably an appropriately substituted acyl chloride (bromide) of formula (2, J=COCl or COBr), in the presence of an inorganic base such as potassium carbonate, or in the presence of an organic base such as pyridine, 4-(dimethylamino)pyridine, or a tertiary amine such as triethylamine or N,N-diisopropyl ethyl amine, in an aprotic solvent such as dichloromethane, N,N-dimethylformamide or tetrahydrofuran, at temperatures ranging from −5° C. to 50° C. to provide the desired compounds of general formula (I) wherein $R_1$ is defined hereinbefore.

Alternatively, the acylating species of formula (2) can be a mixed anhydride of the corresponding carboxylic acid, such as that prepared by treating said acid with 2,4,6-trichlorobenzoyl chloride in an aprotic organic solvent such as dichloromethane according to the procedure of Inanaga et al., Bull. Chem. Soc. Jpn., 52, 1989 (1979). Treatment of said mixed anhydride of general formula (2) with a tricyclic azepine (diazepine) of formula (1) in a solvent such as dichloromethane and in the presence of an organic base such as 4-(dimethylamino)pyridine at temperatures ranging from 0° C. to the reflux temperature of the solvent, yields the acylated derivative (I) of Scheme I.

The acylating intermediate of formula (2) is ultimately chosen on the basis of its compatibility with the $R_1$ groups, and its reactivity with the tricyclic azepine (diazepine) of formula (1).

Likewise, treatment of a bicyclic azepine of formula (3) under conditions similar to those described hereinbefore provides the desired compounds of general formula (II) wherein $R_1$ is defined hereinbefore, as shown in Scheme II.

Scheme II

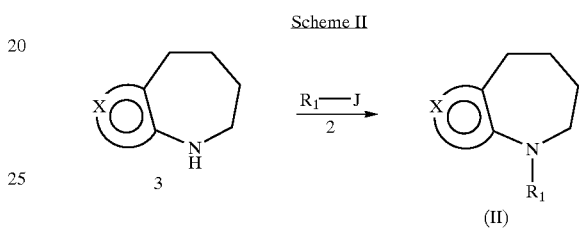

The desired intermediates of formula (2) of Scheme I and II can be conveniently prepared by a process shown in Scheme III. Thus, an appropriately substituted aryl (heteroaryl) iodide (bromide, chloride, or trifluoromethane sulfonate) of formula (4, wherein P is a carboxylic acid protecting group, preferably P=alkyl or benzyl, M=I, Br, Cl, OTf), A is CH or nitrogen, and $R_2$ is defined hereinbefore, is reacted with an aryl(heteroaryl) tri(alkyl)tin(IV) derivative of formula (5, W=Sn(trialkyl)$_3$, preferably Sn(n-Bu)$_3$) wherein $R_7$, $R_8$ and $R_9$ are defined hereinbefore, in the presence of a Pd(0) catalyst and in the presence or absence of inorganic salts (e.g. LiCl), to provide the intermediate ester (6). Subsequent unmasking of the carboxylic acid by hydrolysis, hydrogenolysis or similar methods known in the art, followed by activation of the intermediate acid (7) provides the desired compounds of formula (8) wherein A, $R_2$, $R_7$, $R_8$, and $R_9$ are hereinbefore defined, suitable for coupling with either the tricyclic azepine (diazepine) of formula (1), or with the bicyclic azepine of formula (3), respectively.

Scheme III

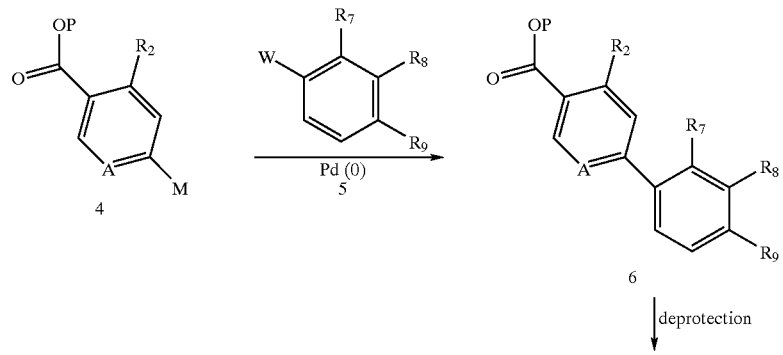

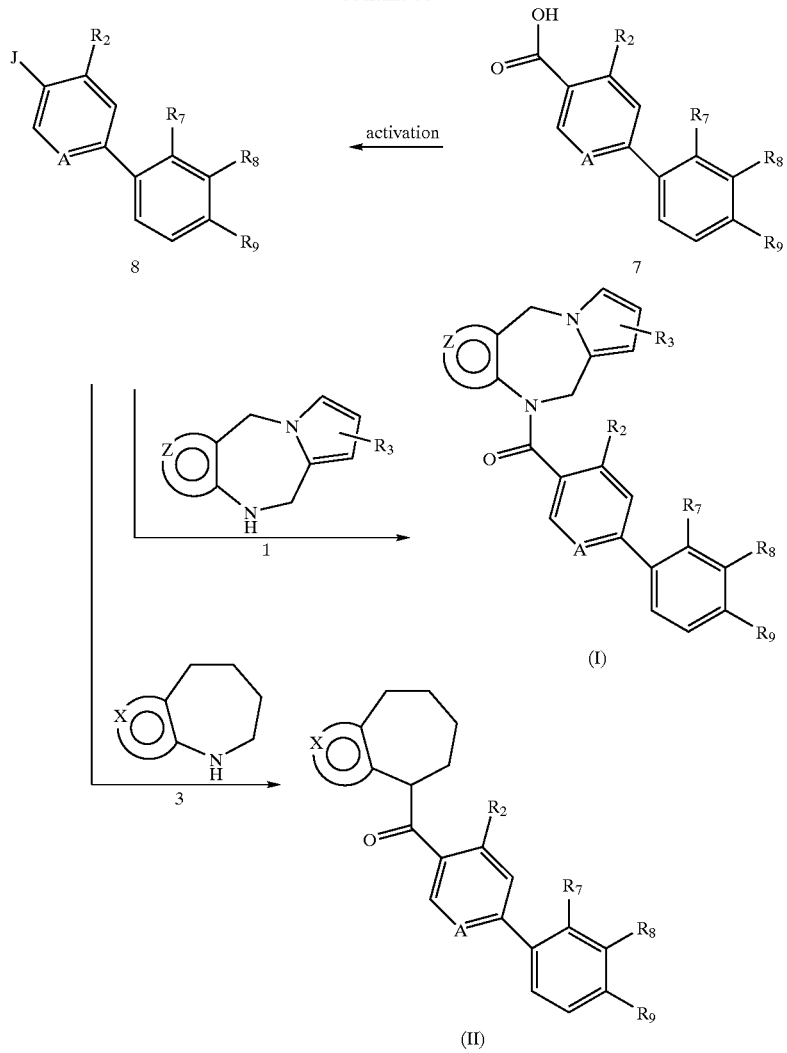

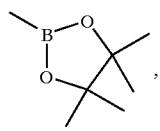

Alternatively, the desired intermediates of formula (6) of Scheme III can be prepared by coupling of the iodide (bromide, chloride, trifluoromethanesulfonate) (4, M=I, Br Cl, or OTf) with an appropriately substituted aryl (heteroaryl) boron derivative of formula (5, preferably W=B(OH)$_2$) in the presence of a palladium catalyst such as palladium(II) acetate or tetrakis(triphenylphosphine) palladium(0) and an organic base such as triethylamine or an inorganic base such as sodium (potassium or cesium) carbonate with or without added tetrabutylammonium bromide (iodide), in a mixture of solvents such as toluene-ethanol-water, acetone-water, water or water-acetonitrile at temperatures ranging from ambient to the reflux temperature of the solvent (Suzuki, *Pure & Appl. Chem.* 66, 213–222 (1994); Badone et al., *J. Org. Chem.* 62, 7170–7173 (1997); Wolfe et al., *J. Am. Chem. Soc.* 121, 9559 (1999); Shen, *Tetr. Letters* 38, 5575 (1997)). The exact conditions for the Suzuki coupling of (4) and the boronic acid intermediate are chosen on the basis of the nature of the substrate and the substituents.

The desired intermediates of formula (6) of Scheme III can be similarly prepared from the bromide (4, M=Br) and the boronic acid (5) in a solvent such as dioxane, in the presence of potassium phosphate and a Pd(0) catalyst.

Alternatively, a cross coupling reaction of an iodide (bromide, chloride, or trifluoromethane sulfonate) of formula (5, W=Br, Cl, I, OTf) with a bis(pinacolato)diboron [boronic acid, or trialkyl tin(IV)] derivative of formula (4, M=

B(OH)$_2$, or SnBu$_3$) yields the desired intermediate of formula (6) which is converted to (I) or (II) in the manner of Scheme III.

The required appropriately substituted aryl(heteroaryl) halides of formula (4, M=Br or I) of Scheme III are either available commercially, or are known in the art or can be readily accessed in quantitative yields and high purity by diazotization of the corresponding substituted anilines (4, P=H, alkyl or benzyl, M=NH$_2$) followed by reaction of the intermediate diazonium salt with iodine and potassium iodide in aqueous acidic medium essentially according to the procedures of Street et al,. *J. Med. Chem.* 36, 1529 (1993)

and Coffen et al., *J. Org. Chem.* 49, 296 (1984) or with copper(I) bromide, respectively (March, *Advanced Organic Chemistry*, 3$^{rd}$ Edn., p.647–648, John Wiley & Sons, New York (1985)).

Alternatively, the desired intermediates of formula (7, A=CH) of Scheme III can be conveniently prepared as shown in Scheme IV by cross-coupling reaction of an appropriately substituted pinacolato borane of formula (11) wherein $R_7$, $R_8$ and $R_9$ are hereinbefore defined, with an aryl triflate of formula (12, Y=OTf) or an aryl halide of formula (12, Y=Br, I) wherein $R_2$ is defined hereinbefore, according to the general procedures of Ishiyama et al., *Tetr. Left.* 38, 3447–3450 (1997) and Giroux et al. *Tetr. Lett.* 38, 3841–3844 (1997), followed by basic or acidic hydrolysis of the intermediate nitrile of formula (13) (cf. March, *Advanced Organic Chemistry*, 3$^{rd}$ Edn., John Wiley & Sons, New York, p. 788 (1985)).

Scheme IV

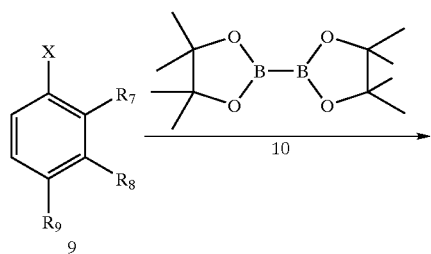

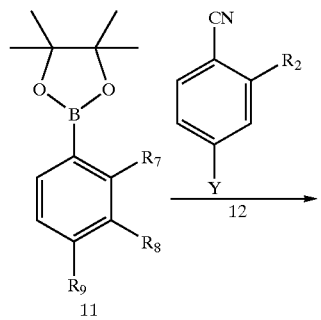

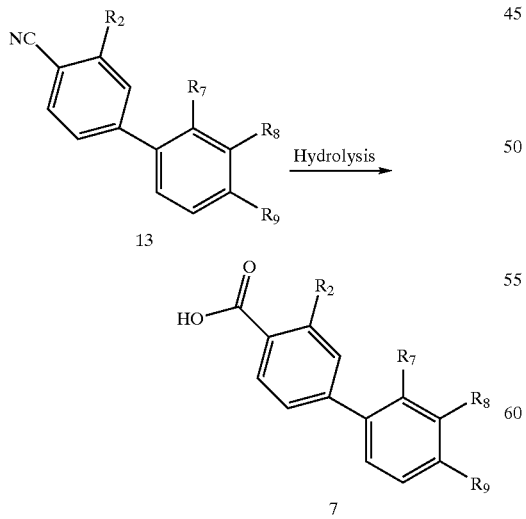

Alternatively, reaction of an iodide (bromide, or trifluoromethanesulfonate) of formula (9, X=Br, I, or OTf) with a bis(pinacolato)diboron [boronic acid or trialkyl tin (IV)] derivative of formula (12,

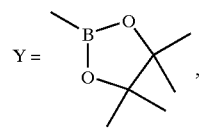

B(OH)$_2$, or SnBu$_3$) yields the desired intermediate of formula (13) which is converted to (7) in the manner of Scheme V.

The desired phenyl boronic esters of formula (11) of Scheme IV can be conveniently prepared by the palladium-catalyzed cross-coupling reaction of the pinacol ester of diboronic acid (10) with an appropriately substituted aryl halide preferably a bromide or iodide (9, X=Br, I) or aryl triflate (9, X=OTf) according to the described procedures of Ishiyama et al., *J. Org. Chem.* 60, 7508–7510 (1995) and Giroux et al., *Tetr. Lett.* 38, 3841–3844 (1997).

The desired compounds of formula (I) of Scheme III can be alternatively prepared by a process shown in Scheme V.

Scheme V

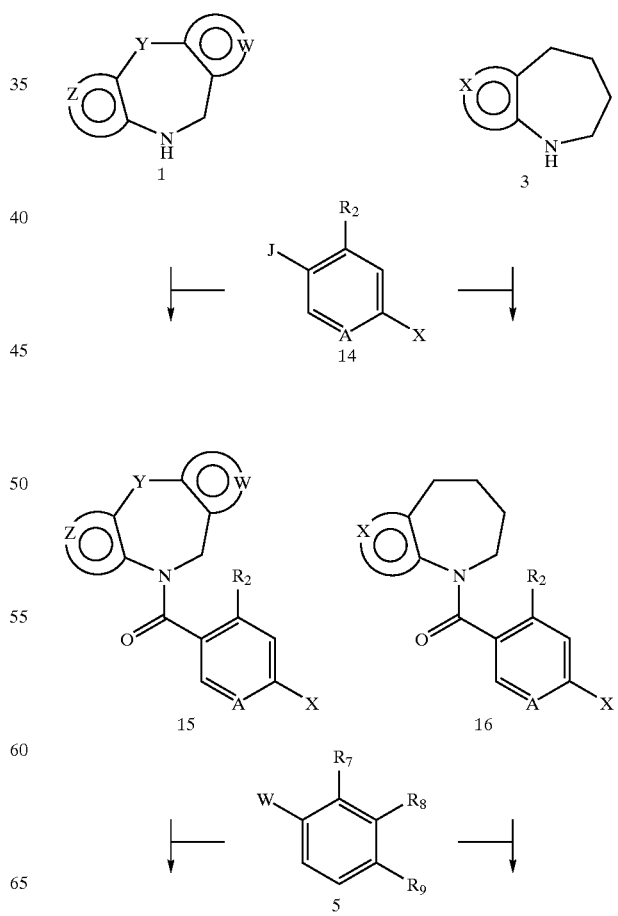

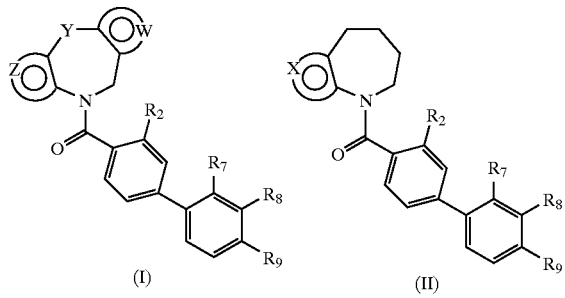

Thus, a tricyclic azepine (diazepine) of formula (1) is treated with an appropriately substituted acylating agent such as a halo aroyl(heteroaroyl)halide, preferably an iodo (bromo) aroyl(heteroaroyl) chloride(bromide) of formula (14, J=COCl or COBr; X=I, Br) wherein A and $R_2$ are hereinbefore defined using any of the procedures hereinbefore described, to provide the acylated intermediate of general formula (15) of Scheme V. In analogous fashion a bicyclic azepine of formula (3) is converted into the desired compounds of formula (16) of Scheme V, using any of the procedures hereinbefore described.

Alternatively, the acylating species of formula (14) can be a mixed anhydride of the corresponding carboxylic acid. Treatment of said mixed anhydride of general formula (14) with either a tricyclic azepine (diazepine) of formula (1) or a bicyclic azepine of formula (3) according to the procedure described hereinbefore, yields the intermediate acylated derivatives (15) and (16), respectively.

The acylating intermediate of formula (14) is ultimately chosen on the basis of its compatibility with A and the $R_2$ group, and its reactivity with the tricyclic azepine (diazepine) of formula (1) or the bicyclic azepine of formula (3), respectively.

A Stille coupling reaction of (15, X=I) or (16, X=I) with an appropriately substituted organotin reagent such as a trialkyltin(IV) derivative, preferably a tri-n-butyltin(IV) derivative of formula (5, W=SnBu$_3$) where $R_7$, $R_8$ and $R_9$ are hereinbefore defined, in the presence of a catalyst such as tetrakis (triphenylphosphine) palladium (0) in an aprotic organic solvent such as toluene or N,N-dimethylformamide, at temperatures ranging from ambient to 150° C. (cf. Farina et al., *J. Org. Chem*, 59, 5905 (1994) and references cited therein) affords the desired compounds of formula (I) or (II) respectively, wherein

Y, A, $R_2$, $R_7$, $R_8$ and $R_9$ are as defined hereinbefore.

Alternatively, the reaction of a compound of formula (15, X=Cl, Br or I) or (16, X=Cl, Br or I) with an appropriately substituted aryl(heteroaryl) boronic acid of formula (5, W=B(OH)$_2$) wherein A, $R_2$, $R_7$, $R_8$, and $R_9$ are hereinbefore defined, in a mixture of solvents such as toluene-ethanol-water, and in the presence of a Pd(0) catalyst and a base such as sodium carbonate, at temperatures ranging from ambient to the reflux temperature of the solvent, yields the desired compounds of formula (I) or (II) respectively, wherein

Y, A, $R_2$,$R_7$, $R_8$, and $R_9$ are as defined hereinbefore.

The preferred substituted aroyl(heteroaroyl) chlorides (bromides) of formula (14) of Scheme V (X=I, Br; J=COCl or COBr) wherein A and $R_2$ are as defined hereinbefore, are either available commercially, or are known in the art, or can be readily prepared by procedures analogous to those in the literature for the known compounds.

The intermediates of formula (5, W=Sn(alkyl)$_3$, preferably alkyl=n-butyl) of Scheme V are either commercially available, or can be conveniently prepared as shown in Scheme VI from the corresponding bromo starting materials of formula (17) wherein $R_7$, $R_8$, and $R_9$ are hereinbefore defined, by first reacting them with n-butyl lithium followed by reaction of the intermediate lithiated species with a trialkyl (preferably trimethyl or tri-n-butyl)tin(IV) chloride.

Scheme VI

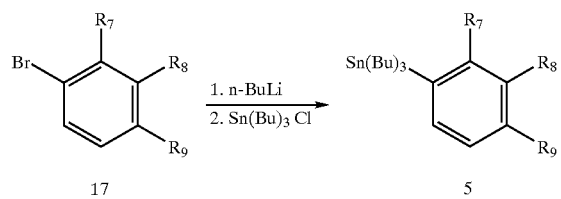

The preferred substituted aryl(heteroaryl) boronic acids of formula (5, W=B(OH)$_2$) are either available commercially, or are known in the art, or can be readily prepared by procedures analogous to those in the literature for the known compounds.

Alternatively, as shown in Scheme VII, the appropriately substituted aroyl(heteroaroyl) halides, preferably aroyl (heteroaroyl) chlorides of formula (18, J=COCl) where A and $R_2$ are hereinbefore defined, are reacted with a tricyclic azepine (diazepine) of formula (1) to provide the intermediate bromides of formula (19). Subsequent reaction of (19) with an hexa alkyl-di-tin (preferably hexa-n-butyl-di-tin (IV)) in the presence of a Pd(0) catalyst such as tetrakis(triphenylphosphine)palladium(0) and lithium chloride, provides the stannane intermediate of formula (20). Further reaction of the tri-n-butyl tin(IV) derivative (20) with the appropriately substituted aryl(heteroaryl) halide of formula (21, M=bromo or iodo) wherein $R_7$, $R_8$, and $R_9$ are hereinbefore defined, in the presence of a Pd(0) catalyst such as tetrakis(triphenylphosphine) palladium(0), yields the desired compounds of formula (I) wherein

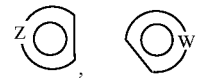

A, Y, $R_2$, $R_7$, $R_8$ and $R_9$ are defined hereinbefore.

Scheme VII

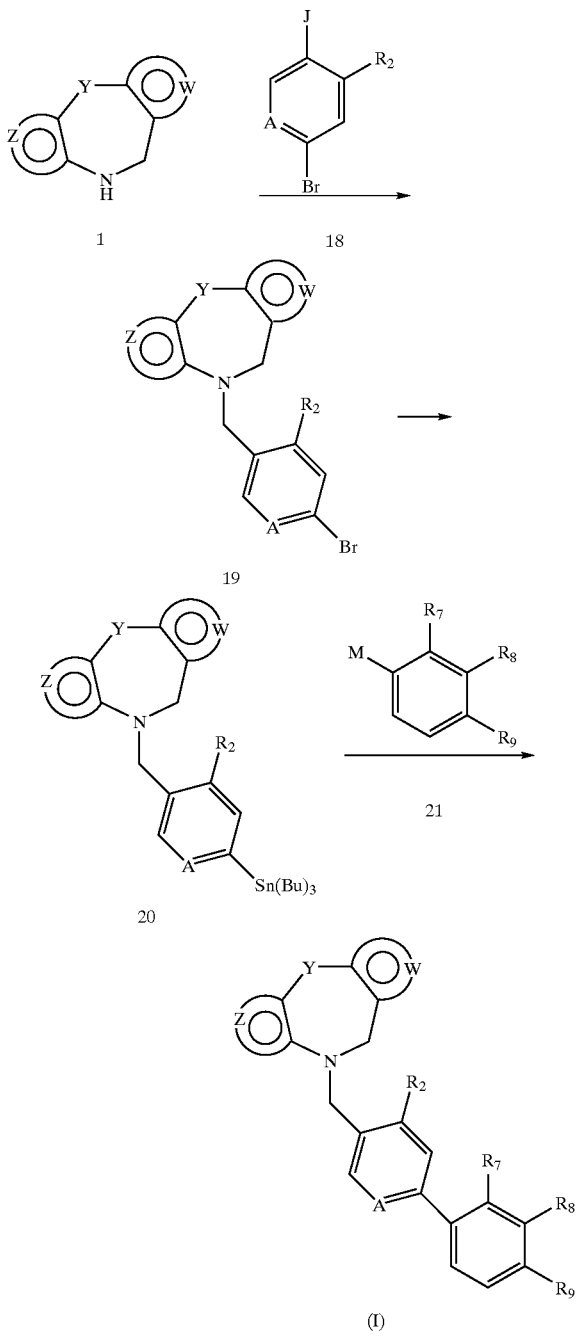

The desired compounds of formula (II) of Scheme II wherein

,

A, $R_2$, $R_7$, $R_8$ and $R_9$ are defined hereinbefore, can be prepared in analogous fashion by reacting a bicyclic azepine of formula (3) with intermediates of formula (18) and (21) according to Scheme VII above.

The subject compounds of the present invention were tested for biological activity according to the following procedures.

Vasopressin $V_2$ Agonist Effects of Test Compounds in Normal Conscious Water-Loaded Rats Male or female normotensive Sprague-Dawley rats (Charles River Laboratories, Inc., Kingston, N.Y.) of 350–500 g body weight were supplied with standard rodent diet (Purina Rodent Lab. Chow 5001) and water ad libitum. On the day of test, rats were placed individually into metabolic cages equipped with devices to separate the feces from the urine and containers for collection of urine. A test compound or a reference agent was given at an oral dose of 10 mg/Kg in a volume of 10 mL/Kg. The vehicle used was 2.5% preboiled corn starch in 20% dimethylsulfoxide (DMSO). Thirty minutes after dosing the test compound, rats were gavaged with water at 30 mL/Kg into the stomach using a feeding needle. During the test, rats were not provided with water or food. Urine was collected for four hours after dosing of the test compound. At the end of four hours, urine volume was measured. Urinary osmolality was determined using a Fiske One-Ten Osmometer (Fiske Associates, Norwood, Mass., 02062) or an Advanced CRYOMATIC Osmometer, Model 3C2 (Advanced Instruments, Norwood, Mass.). Determinations of $Na^+$, $K^+$ and $Cl^-$ ion were carried out using ion specific electrodes in a Beckman SYNCHRON EL-ISE Electrolyte System analyzer. The urinary osmolality should increase proportionally. In the screening test, two rats were used for each compound. If the difference in the urine volume of the two rats was greater than 50%, a third rat was used.

The results of this study are shown in Table 1.

TABLE 1

| Example | Urine Volume (% decrease)[a] | Urinary Osmolality (% increase)[b] | Rat Type[c] |
|---|---|---|---|
| 1 | 67 | 163 | CD |
| 2 | 27 | 33 | CD |
| 3 | 18 | 78 | CD |
| 4 | 56 | 151 | CD |
| 5 | 22 | 26 | CD |
| 6 | 87 | 247 | CD |
| 7 | 70 | 189 | CD |
| 8 | 35 | 73 | CD |
| 9 | 62 | 156 | CD |
| 10 | 60 | 234 | CD |

[a]Percent decrease in urine volume vs control at a dose of 10 mg/Kg
[b]Percent increase in osmolality vs control at a dose of 10 mg/Kg
[c]Rat model used: Sprague-Dawley (CD)

The following examples are presented to illustrate rather than limit the scope of the invention.

EXAMPLE 1

(2'-Methoxy-[1,1'-biphenyl]-4-yl)-(5H,11H-pyrrolo[2,1-c][1,4]benzodiazepin-10-yl)-methanone;

Step A. 2'-Methoxy-[1,1'-biphenyl]-4-carboxylic Acid Ethyl Ester

A mixture of 4-bromo benzoic acid ethyl ester (2.7 mL, 16.5 mmol), 2-methoxy boronic acid (2.5 g, 16.5 mmol) and sodium carbonate (7.7 g, 72.6 mmol) in toluene:ethanol:water (75 mL:37 mL:37 mL), was flushed with nitrogen for 1 hour. After addition of the tetrakis (triphenylphosphine) palladium (0) catalyst (0.96 g, 0.83 mmol), the reaction mixture was heated at 100° C. overnight. After cooling, the mixture was filtered through Celite which was then rinsed with ethyl acetate. The organic layer was washed with water, dried over anhydrous sodium sulfate, filtered and concentrated in vacuo to give a brown oil. Purification of the residue by flash chromatography with a solvent gradient from 25% to 50% dichloromethane in hexane provided the title compound (3.8 g, 89.9%) as a pale yellow oil.

$^1$H-NMR (DMSO-$d_6$, 400 MHz): δ 1.32 (t, 3H), 3.76 (s, 3H), 4.32 (q, 2H), 7.02–7.06 (m, 1H), 7.12–7.14 (m, 1H), 7.31–7.33 (m, 1H), 7.36–7.40 (m, 1H), 7.59–7.63 (m, 2H), 7.96–7.99 (m, 2H).

MS [EI, m/z]: 256 [M]$^+$.

Anal. Calcd. for $C_{16}H_{16}O_3$: C,74.98; H, 6.29. Found: C, 75.11; H, 6.71.

Step B. 2'-Methoxy-[1,1'-biphenyl]-4-carboxylic Acid

A mixture of 2'-methoxy-[1,1'-biphenyl]-4-carboxylic acid ethyl ester of Step A (3.7 g, 14.4 mmol) in tetrahydrofuran (40 mL) and 1 N sodium hydroxide (30 mL, 30 mmol) was heated at reflux overnight. After cooling, the reaction mixture was concentrated in vacuo, and the residue was acidified with 2N hydrochloric acid to give a white solid which was collected by filtration and dried under vacuum to provide the title compound (3.2 g, 97.4%) as a white solid, m.p. 250–253° C.

$^1$H-NMR (DMSO-$d_6$, 400 MHz): δ 3.78 (s, 3H), 7.04–7.08 (m, 1H), 7.13–7.16 (m, 1H), 7.32–7.35 (m, 1H), 7.37–7.41 (m, 1H), 7.59–7.62 (m, 2H), 7.96–7.99 (m, 2H), 12.92 (broad s, 1H).

MS [EI, m/z]: 228 [M]$^+$.

Anal. Calcd. for $C_{14}H_{12}O_3$+0.01$CH_2Cl_2$+0.04$C_4H_8O$: C, 73.34; H, 5.39. Found: C, 72.74; H, 5.46.

Step C. (2'-Methoxy-[1,1'-biphenyl]-4-yl)-(5H,11H-pyrrolo[2,1-c][1,4]benzodiazeopin-10-yl)-methanone A suspension of 2'-methoxy-[1,1'-biphenyl]-4-carboxylic acid of Step B (1.0 g, 4.38 mmol) in thionyl chloride (6 mL) was heated at reflux for 30 min. After cooling, the thionyl chloride was removed in vacuo. The residue was dissolved in toluene and concentrated in vacuo to give the crude acid chloride as a yellow solid. The latter was then dissolved in dichloromethane (10 mL) and the solution was slowly added to a solution of 10,11-dihydro-5H-pyrrolo [2,1-c][1,4]benzodiazepine (0.97 g, 5.27 mmol) and N,N-diisopropylethyl amine (1.6 mL, 9.19 mmol) in dichloromethane (30 mL). After stirring for 2 hours, the reaction was quenched with water. The organic layer was washed with 1 N hydrochloric acid, 1 N sodium hydroxide and brine, dried over anhydrous sodium sulfate, filtered and concentrated in vacuo to give a yellow foam. Purification of the residue by flash chromatography using a solvent gradient from 15% to 25% of ethyl acetate in hexane provided the title compound as a white foam which was crystallized by sonication from ethyl acetate/hexane (1.4 g, 81.0%) to give a white solid m.p. 145–147° C.

$^1$H-NMR (DMSO-$d_6$, 400 MHz): δ 3.71 (s, 3H), 4.80–5.40 (broad s, 4H), 5.92–5.93 (m, 1H), 5.95 (s, 1H), 6.82 (t, 1H), 6.96–7.00 (m, 2H), 7.08 (d, 1H), 7.12–7.21 (m, 3H), 7.29–7.35 (m, 5H), 7.47–7.49 (m, 1H)

MS [(+)ESI, m/z]: 395 [M+H]$^+$.

Anal. Calcd. for $C_{26}H_{22}N_2O_2$+0.08$C_4H_8O_2$: C, 78.73; H, 5.68; N 6.98. Found: C, 78.47; H, 5.77; N, 7.00.

EXAMPLE 2

(10,11-Dihydro-5H-pyrrolo[2,1-c][1,4]benzodiazepin-10-yl)-(3'-methyl-[1,1'-biphenyl]-4-yl)-methanone Step A. 3'-Methyl-[1,1'-biphenyl]-4-carboxylic Acid Ethyl Ester A mixture of 4-bromo benzoic acid ethyl ester (2.7 mL, 16.5 mmol), 3-methyl phenylboronic acid (2.2 g, 16.2 mmol) and sodium carbonate (7.5 g, 70.8 mmol) in toluene:ethanol:water (75 mL:37 mL:37 mL), was flushed with nitrogen for 1 hour. After addition of the tetrakis (triphenylphosphine) palladium(0) catalyst (0.94 g, 0.81 mmol), the reaction was heated at 100° C. overnight. After cooling, the mixture was filtered through Celite which was then washed with ethyl acetate. The organic layer was washed with water, dried over anhydrous sodium sulfate, filtered and concentrated in vacuo to give a brown oil. Purification of the residue by flash chromatography with a solvent gradient from 25% to 50% of dichloromethane in hexane provided the title compound (3.4 g, 87.3%) as a colorless oil.

$^1$H-NMR (DMSO-$d_6$, 400 MHz): δ 1.34 (t, 3H), 2.39 (s, 3H), 4.34 (q, 2H), 7.23–7.25 (m, 1H), 7.39 (t, 1H), 7.51–7.55 (m, 2H), 7.79–7.82 (m, 2H), 8.01–8.04 (m, 2H).

MS [EI, m/z]: 240 [M]$^+$.

Anal. Calcd. for $C_{16}H_{16}O_2$: C, 79.97; H, 6.71. Found: C, 79.54; H, 6.71.

Step B. 3'-Methyl-[1,1'-biphenyl]-4-carboxylic Acid

A solution of 3'-methyl-[1,1'-biphenyl]-4-carboxylic acid ethyl ester of Step A (3.3 g, 13.7 mmol) in tetrahydrofuran (40 mL) and 1 N sodium hydroxide (27.5 mL, 27.5 mmol) was heated at reflux overnight. After cooling, the reaction was concentrated in vacuo. The residue was acidified with 2N hydrochloric acid to yield a white solid which was collected by filtration and dried under vacuum to provide the title compound (2.9 g, 99.7%) as a white solid, m.p. 198–200° C.

$^1$H-NMR (DMSO-$d_6$, 400 MHz): δ 2.39 (s, 3H), 7.24 (d, 1H), 7.39 (t, 1H), 7.51–7.56 (m, 2H), 7.77–7.80 (m, 2H), 8.00–8.03 (m, 2H), 12.96 (broad s, 1H).

MS [EI, m/z]: 212 [M]$^+$.

Anal. Calcd. for $C_{14}H_2O_2$: C, 79.22; H, 5.70. Found: C, 78.82; H, 5.87.

Step C. (10,11-Dihydro-5H-pyrrolo[2,1-c][1,4]benzodiazepin-10-yl)-(3'-methyl-[1,1'-biphenyl]-4-yl)-methanone A suspension of 3'-methyl-[1,1'-biphenyl]-4-carboxylic acid of Step B (0.50 g, 2.36 mmol) in thionyl chloride (3 mL) was heated at reflux for 30 minutes. After cooling, the thionyl chloride was removed in vacuo. The residue was dissolved in toluene and concentrated in vacuo to give the crude acid chloride as a yellow oil. The acid chloride was then dissolved in dichloromethane (5 mL) and slowly added to a solution of the 10,11-dihydro-5H-pyrrolo [2,1-c][1,4]benzodiazepine (0.65 g, 3.53 mmol) and N,N-diisopropylethyl amine (0.90 mL, 5.17 mmol) in dichloromethane (15 mL). After stirring for 2 hours, the reaction was quenched with water. The organic layer was washed with 1 N hydrochloric acid, 1 N sodium hydroxide and brine, dried over anhydrous sodium sulfate, and concentrated in vacuo to give a white foam. Purification of the residue by flash chromatography using a solvent gradient from 15% to 25% of ethyl acetate in hexane gave a white foam which was crystallized by sonication from ethyl acetate/hexane to provide the title compound (0.74 g, 82.8%) as a white solid, m.p. 128–130° C.

$^1$H-NMR (DMSO-$d_6$, 400 MHz): δ 2.35 (s, 3H), 4.80–5.40 (broad s, 4H), 5.93–5.95 (m, 1H), 5.97 (s, 1H), 6.85 (t, 1H), 6.96–6.98 (m, 1H), 7.12 (t, 1H), 7.17–7.21 (m, 2H), 7.30–7.44 (m, 5H), 7.48–7.54 (m, 3H).

MS [EI, m/z]: 378 [M]$^+$.

Anal. Calcd. for $C_{26}H_{22}N_2O$+0.10$C_4H_8O_2$: C, 81.88; H, 5.93; N, 7.23. Found: C, 81.54; H, 5.99; N, 7.29.

EXAMPLE 3

(10,11-Dihydro-5H-pyrrolo[2,1-c][1,4]benzodiazepin-10-yl)-(4'-methoxy[1,1'-biphenyl]-4-yl)-methanone Step A. 4'-Methoxy-[1,1'-biphenyl]-4-carboxylic Acid Ethyl Ester A mixture of 4-bromobenzoic acid ethyl ester (2.7 mL, 16.5 mmol), 4-methoxy phenylboronic acid (2.5 g, 16.5 mmol) and sodium carbonate (7.7 g, 72.6 mmol) in toluene:ethanol:water (75 mL:37 mL:37 mL) was flushed with nitrogen for 1 hour. After addition of the tetrakis (triphenylphosphine) palladium (0) catalyst (0.95 g, 0.82 mmol), the reaction was heated at 100° C. overnight. After cooling, the mixture was filtered through Celite which was then washed with ethyl acetate. The organic layer was washed with water, dried over anhydrous sodium sulfate, filtered and concentrated in vacuo to give a brown solid. Purification of the residue by flash chromatography with a solvent gradient from 25% to 50% of dichloromethane in hexane provided the title compound (4.05 g, 95.8%) as a pale yellow solid, m.p. 101–103° C.

$^1$H-NMR (DMSO-$d_6$, 400 MHz): δ 1.34 (t, 3H), 3.81 (s, 3H), 4.33 (q, 2H), 7.05–7.07 (m, 2H), 7.69–7.71 (m, 2H), 7.77–7.79 (m, 2H), 7.98–8.01 (m, 2H).

MS [EI, m/z]: 256 [M]$^+$.

Anal. Calcd. for $C_{16}H_{16}O_3$: C, 74.98; H, 6.29. Found: C, 74.92; H, 6.16.

Step B. 4'-Methoxy-[1,1'-biphenyl]-4-carboxylic Acid

A solution of the ester of Step A (3.9 g, 15.2 mmol) in tetrahydrofuran (50 mL) was treated with 1 N sodium hydroxide (31 mL, 31 mmol) and then heated at reflux overnight. After cooling, the reaction mixture was concentrated in vacuo. The residue was acidified with 2N hydrochloric acid to give a white solid which was collected by filtration and dried under vacuum to provide the title compound (3.4 g, 98.0%) as a white solid, m.p. 250–254° C.

$^1$H-NMR (DMSO-$d_6$, 400 MHz): δ 3.81 (s, 3H), 7.04–7.08 (m, 2H), 7.68–7.71 (m, 2H), 7.73–7.77 (m, 2H), 7.98–8.01 (m, 2H), 12.91 (broad s, 1H).

MS [(−)ESI, m/z]: 227 [M−H]$^−$.

Anal. Calcd. for $C_{14}H_{12}O_3$: C, 73.67, H, 5.30. Found: C, 73.11, H, 5.41.

Step C. (10,11-Dihydro-5H-pyrrolo[2,1-c][1,4]benzodiazepin-10-yl)-(4'-methoxy-[1,1'-biphenyl]-4-yl)-methanone A suspension of the carboxylic acid of Step B (1.0 g, 4.38 mmol) in thionyl chloride (6 mL) was heated at reflux for 1 hour. After cooling, the thionyl chloride was removed in vacuo. The residue was dissolved in toluene and concentrated in vacuo to give the crude acid chloride as a light brown solid. The acid chloride was then dissolved in dichloromethane (10 mL) and slowly added to a solution of 10,11-dihydro-5H-pyrrolo [2,1-c][1,4]benzodiazepine (1.2 g, 6.52 mmol) and N,N-diisopropylethyl amine (1.7 mL, 9.76 mmol) in dichloromethane (25 mL). After stirring for 2 hours, the reaction was quenched with water. The organic layer was washed with 1N hydrochloric acid, 1N sodium hydroxide and brine, dried over anhydrous sodium sulfate, filtered and concentrated in vacuo to give a yellow foam. Purification of the residue by flash chromatography using a solvent gradient from 15% to 50% of ethyl acetate in hexane provided the title compound (1.5 g, 86.8%) as a white solid, m.p. 187–189° C.

$^1$H-NMR (DMSO-$d_6$, 400 MHz): δ 3.76 (s, 3H), 4.80–5.40 (broad s, 4H), 5.92–5.94 (m, 1H), 5.96 (s, 1H), 6.83 (t, 1H), 6.94–6.99 (m, 3H), 7.10 (t, 1H), 7.15–7.19 (m, 1H), 7.32 (d, 2H), 7.47–7.49 (m, 3H), 7.55–7.58 (m, 2H).

MS [(+)ESI, m/z]: 395 [M+H]$^+$.

Anal. Calcd. for $C_{26}H_{22}N_2O_2$+0.20 $CH_2Cl_2$: C, 76.48; H, 5.49; N, 6.81. Found: C, 76.10; H, 5.68; N, 6.87.

EXAMPLE 4

[1,1'-Biphenyl]-4-yl-(5,11-dihydro-benzo[b]pyrido[2,3-e][1,4]diazepin-6-yl)-methanone To a solution of 6,11-dihydro-5H-pyrido [2,3-b][1,5]benzodiazepine (1.0 g, 5.07 mmol) in N,N-dimethylformamide (10 mL) kept under nitrogen was added solid potassium carbonate (0.74 g, 5.35 mmol). The mixture was treated dropwise with a solution of 4-biphenylcarbonyl chloride (1.4 g, 6.46 mmol) in N,N-dimethylformamide (5 mL) and stirred at room temperature for 1 hour. The mixture was then diluted with water and extracted with ethyl acetate. The organic extracts were combined and washed with 1N sodium hydroxide, dried over anhydrous sodium sulfate and evaporated to dryness to give a pink foam which was purified by flash chromatography. Elution with 25% ethyl acetate in hexane provided a white foam which was redissolved in dichloromethane, concentrated in vacuo to a foam, then crystallized by sonication from ethyl acetate/hexane to give the title compound (1.28 g, 66.9%) as a white solid, m.p. 175–177° C.

$^1$H-NMR (DMSO-$d_6$, 400 MHz): δ 4.11 (d, 1H), 5.60 (d, 1H), 6.53–6.59 (m, 1H), 6.68–6.70 (m, 1H), 6.72–6.78 (m, 1H), 7.04–7.09 (m, 1H), 7.20 (d, 2H), 7.32–7.36 (m, 2H), 7.37–7.43 (m, 2H), 7.48–7.61 (m, 5H), 8.10–8.12 (m, 1H), 9.62 (s, 1H).

MS [(+)ESI, m/z]: 378 [M+H]$^+$.

Anal. Calcd. for $C_{25}H_{19}N_3O$+0.05 $C_4H_8O_2$+0.05 $CH_2Cl_2$: C 78.55, H 5.09, N, 10.88. Found: C, 78.55; H, 4.90; N 10.87.

EXAMPLE 5

[1,1'-Biphenyl]-4-yl-(11-methyl-5,11-dihydro-benzo[b]pyrido[2,3-e][1,4]diazepin-6-yl)-methanone Sodium hydride (60% suspension, 0.10 g, 2.5 mmol) washed with hexane and dried under nitrogen, was suspended in dry N,N-dimethylformamide (15 mL). Following addition of 1,1'-biphenyl-4-yl-(5,11-dihydro-benzo[b]pyrido[2,3-e][1,4]diazepin-6-yl)-methanone of Example 4 (0.76 g, 2.0 mmol), methyl iodide (0.5 mL, 2.4 mmol) was added. After stirring for 1 hour, the reaction was quenched with water and extracted with dichloromethane The organic layers were dried over anhydrous sodium sulfate and concentrated in vacuo to give a yellow solid. Purification of the residue by flash chromatography using a solvent gradient from 25% to 35% of ethyl acetate in hexane gave a white foam which was redissolved in dichloromethane, concentrated in vacuo to a foam, then crystallized by sonication from ethyl acetate/hexane to provide the title compound (0.48 g, 61.3%) as a white solid, m.p. 220–223° C.

$^1$H-NMR (DMSO-$d_6$, 400 MHz): δ 3.55 (s, 3H), 4.28–46.40 (broad m, 1H), 5.70–5.85 (broad m, 1H), 6.88–6.97 (m, 2H), 7.02–7.05 (m, 1H), 7.26 (t, 1H), 7.32–7.38 (m, 4H), 7.43 (t, 2H), 7.55–7.63 (m, 5H), 8.22–8.24 (m, 1H).

MS [(+) APCI, m/z]: 392 [M+H]$^+$.

Anal. Calcd. for $C_{26}H_{21}N_3O$+0.04 $C_4H_8O_2$+0.20 $CH_2Cl_2$: C, 76.85; H, 5.31, N, 10.20.

Found: C, 76.99; H, 5.20; N, 9.98.

EXAMPLE 6

[1,1'-Biphenyl]-4-yl-(5,11-dihydro-10H-dibenzo[b,e][1,4]diazepin-10-yl)methanone 4-Biphenyl-carbonyl chloride (1.19 g) dissolved in N,N-dimethylformamide (10 mL) was added dropwise to an ice cooled solution of 5,11-dihydro-10H-dibenzo[b,e][1,4]

diazepine (0.98 g) in N,N-dimethylformamide (10 mL). After stirring at room temperature overnight, the reaction mixture was poured into water and dichloromethane. The organic layer was sequentially washed with water and saturated sodium bicarbonate, and dried over anhydrous sodium sulfate. The solution was filtered through a short column of Magnesol® and eluted with additional dichloromethane. The combined eluate was refluxed with gradual addition of hexane until incipient crystallization occurred. Cooling and filtration provided the title compound (0.72 g), m.p. 180–182° C.

Anal. Calcd. for $C_{26}H_{20}N_2O$: C, 82.95; H, 5.35; N, 7.44. Found: C, 82.84; H, 5.24; N, 7.40.

EXAMPLE 7
[1,1'-Biphenyl]-4-yl-(5-methyl-5,11-dihydro-10H-dibenzo[b,e][1,4]diazepin-10-yl)methanone

[1,1'-Biphenyl]-4-yl-(5,11-dihydro-10H-dibenzo[b,e][1,4]diazepin-10-yl)methanone of Example 6 (0.97 g) was added to sodium hydride (2 equivalents, 60% in oil, washed with hexane) and N,N-dimethylformamide (25 mL). Iodomethane (0.45 g) was added and after overnight stirring, the mixture was poured into brine. The precipitate was collected, redissolved in dichloromethane and the solution filtered through a short column of Magnesol®. The column was rinsed with several volumes of dichloromethane, and the combined eluate refluxed with the gradual addition of hexane until incipient crystallization. Cooling and filtration provided the title compound (0.89 g), m.p. 198–201° C.

MS [(+)ESI, m/z]: 391 [M+H]$^+$.

EXAMPLE 8
[1,1'-Biphenyl]-4-yl-(5,6,7,8-tetrahydro-thieno[3,2-b]azepin-4-yl)-methanone Step A. 5,6,7,8-Tetrahydro-4H-thieno-[3,2-b]azepine A solution of 6,7-dihydro-5H-benzo[b]thiophen-4-one oxime (1.67 g) in dry dichloromethane (100 mL) was cooled to 0°. Following dropwise addition of diisobutylaluminum hydride (50 ml, 1 M in hexanes), the mixture was stirred at 0° for three hours and then diluted with dichloromethane (50 mL). Sodium fluoride (8.4 g) was added, followed by water (2.7 mL). The reaction mixture was stirred vigorously for 30 minutes, then filtered, and concentrated to provide the title compound (0.81 g) as a white solid.

$^1$H-NMR (200 mHz, CDCl$_3$): δ 1.70 (m, 2H), 1.87 (m, 2H), 2.75 (m, 2H), 3.05 (m, 2H), 3.50 (brs, 1H), 6.51 (d, 1H), 6.82 (d, 1H).

Step B. 1,1'-Biphenyl-4-yl-(5,6,7,8-tetrahydro-thieno[3,2-b]azepin-4-yl)-methanone A solution of 5,6,7,8-tetrahydro-4H-thieno[3,2-b]azepine of Step A (0.300 g) and N,N-diisopropylethyl amine (0.5 mL) in dichloromethane (25 mL) was cooled to 0°. To this was added a solution of 4-biphenyl carbonyl chloride (0.518 g) in dichloromethane (5 ml). The solution was stirred overnight as it warmed to room temperature, then washed with 0.1N hydrochloric acid, aqueous sodium bicarbonate and brine. The organic layer was dried over anhydrous sodium sulfate, filtered and evaporated to an oil. Flash chromatography of the residue on silica gel provided the title compound as a white solid (0.490 g), m.p. 164–166° C.

IR (KBr, cm$^{-1}$): 1630

NMR (400 mHz, DMSO-d$_6$): δ 1.82 (br, 2H), 2.04 (br, 2H), 2.95 (dd, 2H), 3.90 (br, 2H), 6.23 (br s, 1H), 6.65 (br s, 1H), 7.34, (m, 3H), 7.43, (m, 4H), 7.55 (dd, 2H).

MS [EI,m/z]: 333 [M]$^+$.

Anal Calcd for $C_{21}H_{19}NOS$: C, 75.64; H, 5.74; N, 4.20. Found: C 75.37; H 5.79; N 4.12.

EXAMPLE 9
(5H,11H-Benzo[e]pyrrolo[1,2-a][1,4]diazepin-10-yl)-(6-phenyl-pyridin-3-yl)-methanone A suspension of 5H,11H-benzo[e]pyrrolo[1,2-a][1,4]diazepin-10-yl)-(6-chloro-pyridin-3-yl)-methanone (0.323 g) and phenyl boronic acid (0.185 g) in a mixture of toluene/1M aqueous sodium carbonate/ethanol (6 mL/2 mL/1 mL) was sparged with nitrogen for 5 minutes. To the stirred mixture was added palladium(II) acetate (0.0135 g). The reaction was then heated to reflux under a static pressure of nitrogen for 14 hours. The suspension was diluted with ethyl acetate and washed with saturated aqueous sodium bicarbonate and brine. The organic layer was dried over anhydrous sodium sulfate, filtered and evaporated in vacuo to yield a green foam (0.360 g). Flash chromatography of the residue on Merck silica gel eluting with 25% ethyl acetate in hexanes provided the title compound (0.250 g) as a white foam which was recrystallized from acetone/hexane to give yellow needles, m.p. 171–174° C.

$^1$H-NMR (DMSO-d$_6$, 400 mHz): δ 5.37 (brs, 2H), 5.92 (t, 1H), 5.97 (s, 1H), 6.83 (t, 1H), 7.03 (d, 1H), 7.10 (t, 1H), 7.19 (t, 1H), 7.45 (m, 4H), 7.75 (d, 1H), 7.85 (d, 1H), 8.02 (dd, 2H), 8.48 (br, 1H)

Anal Calcd for $C_{24}H_{19}N_3O$ 0.25 $H_2O$: C, 77.70; H, 5.31; N, 11.36. Found: C, 77.70; H, 5.23; N, 11.39.

EXAMPLE 10
(5H,11H-Benzo[e]pyrrolo[1,2-a][1,4]diazepin-10-yl)-(4'-methoxy-3-methyl-[1,1'-biphenyl]-4-yl)-methanone Step A. 4'-Methoxy-3-methyl-[1,1'-biphenyl]-4-carboxylic Acid 4-Bromo-2-methyl-benzoic acid (2.15 g, 10 mmol), 4-methoxy-phenylboronic acid (1.52 g, 10 mmol) and sodium carbonate (3.24 g, 30 mmol) in a mixture of toluene, water and ethanol (15 mL:6 mL:3 mL) was sparged with nitrogen for 5 minutes. To this was added palladium acetate (0.014 g). The mixture was heated at reflux, under a static pressure of nitrogen, for 24 hours. The sample was diluted with water and ethyl acetate (50 mL each) and the pH was adjusted to 1. The layers were separated and the aqueous phase was extracted with ethyl acetate. The organic extracts were combined and washed with water and brine. The sample was dried over anhydrous sodium sulfate, filtered and concentrated in vacuo. The resulting solid was recrystallized from ethyl acetate/hexanes to yield the title compound (2.16 g ) as a white solid, m.p 199–201° C.

$^1$H NMR (DMSO-d$_6$, 400 MHz): δ 2.57 (s, 3H), 3.79 (s, 3H), 7.02 (m, 2H), 7.21 (dd, 1H); 7.55 (s, 1H); 7.67 (m, 2H); 7.87 (d, 1H); 12.73 (s, 1H)

MS [EI, m/z]: 242 [M]$^+$.

Anal. Calc'd for $C_{15}H_{14}O_3$: C, 74.36; H, 5.82. Found: C, 73.92; H, 5.93.

Step B. (5H,11H-Benzo[e]pyrrolo[1,2-a][1,4]diazepin-10-yl)-(4'-methoxy-3-methyl-[1,1'-biphenyl]-4-yl)-methanone A mixture of the 4'-methoxy-3-methyl-biphenyl-4-carboxylic acid of Step A (0.486 g, 2 mmol) and thionyl chloride (3 mL) was stirred for 30 minutes and then warmed to reflux for 15 minutes. The reaction product was dissolved in toluene (10 mL) and concentrated in vacuo. This process was repeated twice to provide the crude acid chloride. This was dissolved in dichloromethane (10 mL) and the solution added dropwise to a cooled solution (0°) of 10,11-dihydro-5H-benzo[e]pyrrolo[1,2-a][1,4]diazepine (0.368 g, 2 mmol), triethylamine (0.4 mL, 2.8 mmol) and a catalytic amount of 4-(dimethylamino)pyridine. The solution was stirred overnight at room temperature and then quenched with 1N hydrochloric acid. The mixture was diluted with water and dichloromethane and the organic layer washed with 0.1N hydrochloric acid, 0.1N sodium hydroxide, and water. The solution was dried over anhydrous sodium sulfate and concentrated to a foam. The residue was flash chromatographed on with 30% ethyl acetate in hexane to yield a foam (0.700 g), which upon, trituration and sonication with ether and a little ethyl acetate provided the title compound (0.600 g) as a white solid.

$^1$H-NMR (DMSO-$d_6$, 400 MHz): δ 2.37 (s, 3H), 3.76 (s, 3H), 5.10 (br s, 2H), 5.25 (br s, 2H), 5.90 (t, 1H), 5.96 (brs, 1H), 6.8–7.6 (m, 12H)

MS [(+)ESI, m/z]: 409 [M+H]$^+$.

Anal. Calc'd for $C_{27}H_{24}N_2O_2$: C, 79.39; H, 5.92; N, 6.86. Found: C, 78.51, H, 5.98, N, 6.66.

EXAMPLE 11

[1,1'-Biphenyl]-4-yl-(4H,10H-3a,5,9-triaza-benzo[f]azulen-9-yl)-methanone

Step A. 2-Chloromethyl-pyridine-3-carboxylic Acid Methyl Ester

A solution of methyl 2-methylnicotinate (20.0 g, 0.132 mol) and trichloroisocyanuric acid (46.0 g, 0.198 mol) in dichloromethane (100 mL) was stirred at room temperature overnight. The reaction mixture was then washed with saturated aqueous sodium carbonate and saturated aqueous sodium chloride, dried over anhydrous magnesium sulfate, filtered, and the solvent evaporated in vacuo to provide the title compound as a yellow liquid (11.2 g), which is used as such in the next step.

Step B. 2-(2-Formyl-pyrrol-1-ylmethyl)-pyridine-3-carboxylic Acid Methyl Ester

To a suspension of sodium hydride (5.8 g, 0.12 mol), in dry N,N-dimethyl formamide (25 mL) was added slowly under nitrogen a solution of pyrrole 2-carboxaldehyde (10.5 g, 0.11 mol) in N,N-dimethylformamide (10 mL), and the reaction mixture was stirred at room temperature for 30 minutes. The reaction was then cooled to 5° C. and 2-chloromethyl-pyridine-3-carboxylic acid methyl ester of Step A was added slowly, the temperature being maintained at or below 20° C. After the addition was complete, the reaction was stirred at room temperature for 30 minutes. The mixture was evaporated to dryness, and the residue was dissolved in ethyl acetate (250 mL). This solution was washed with water and dried over anhydrous magnesium sulfate. The solvent was then removed in vacuo leaving a dark crystalline solid (23.4 g), which was purified by chromatography on silica gel eluting with a gradient of ethyl acetate/petroleum ether to provide the title compound as a tan crystalline solid (13.75 g), m.p. 91–93° C.

Step C. [3-(2-Formyl-pyrrol-1-yl-methyl)-pyridin-2-yl]-carbamic acid benzyl ester To a stirred solution of 2-(2-formyl-pyrrol-1-ylmethyl)-pyridine-3-carboxylic acid methyl ester of Step B (13.65 g, 55.9 mmol) in methanol (50 mL) was added sodium hydroxide (2.2 g, 55.9 mmol.). The reaction mixture was refluxed under nitrogen for 2 hours, and then the solvent was removed in vacuo. A portion of the residual yellow solid (5 g) was suspended in a mixture of benzyl alcohol (20 mL) and benzene (30 mL). Diphenylphosphoryl azide (6.54 g, 1.2 equiv.) was added, and the reaction was slowly heated to reflux. After refluxing for 1 hour, the mixture was cooled and washed with water, dried over anhydrous magnesium sulfate, filtered and evaporated to dryness to provide the title compound as a tan crystalline solid (4.4 g), m.p. 109–111° C.

Step D. 9,10-Dihydro-4H-3a,5,9-triaza-benzo[f]azulene

A stirred mixture of [3-(2-formyl-pyrrol-1-yl-methyl)-pyridin-2-yl]-carbamic acid benzyl ester of step B (1.0 g), in ethyl acetate (10 mL) containing 10% palladium on charcoal (10 mg.), magnesium sulfate (0.010 g) and 5 drops of acetic acid was hydrogenated at atmospheric pressure until hydrogen uptake ceased. The reaction mixture was then filtered through Celite and the solvent removed in vacuo. The crude product (yellow crystalline solid, 0.530 g) was purified by chromatography on silica gel eluting with a gradient of ethyl acetate in petroleum ether to provide the title product as a yellow crystalline solid, m.p. 171–172° C.

Step E. 1,1'-Biphenyl-4-yl-(4H, 10H-3a,5,9-triaza-benzo[f] azulen-9-yl)-methanone A stirred mixture of 9,10-dihydro-4H-3a, 5, 9-triazabenzo[f]azulene of Step D (0.54 mmol), 4-phenylbenzoylchloride (1.08 mmol) and triethylamine (1.08 mmol) in toluene was refluxed under nitrogen for 72 hours. The reaction was cooled and the solvent removed in vacuo. Chromatography of the residue over silica gel Merck-60 with a solvent gradient from 5 to 20% ethyl acetate in hexane provided the title compound as a tan solid.

$^1$H-NMR (DMSO-$d_6$, 400 MHz): δ 5.1 (bs, 2H), 5.4 (s, 2H), 5.9 (m, 1H), 6.0 (s, 1H), 6.9 (m, 1H), 7.1 (m, 1H), 7.3–8.7 (m, 10H), 8.3 (m, 1H).

MS [APCI, m/z]: 366 [M+H]$^+$.

Anal. Calcd. for $C_{24}H_{19}N_3O+0.5\ H_2O$: C 76.99, H 5.38, N 11.22. Found: C 77.28, H 5.22, N 10.71.

The following examples were prepared according to the General Procedure A described below.

General Procedure A

Step A. An optionally substituted haloaryl carboxylic acid (1.1 mol) was converted to the acid chloride by treatment with oxalyl chloride (1.5 mmol) and a catalytic amount of N,N-dimethylformamide in dichloromethane. Upon consumption of the acid as determined by HPLC analysis, all volatiles were removed in vacuo. The residue was dissolved in dichloromethane and added dropwise to a stirred and cooled (0° C.) solution of an appropriately substituted 10,11-dihydro-5H-pyrrolo[2,1-c][1,4]benzodiazepine, 11-methyl-6,11-dihydro-5H-pyrido[2,3-b][1,5] benzodiazepine, or 5-methyl-5,11-dihydro-10H-dibenzo[b, e][1,4]diazepine (1 mmol) respectively, and N,N-diisopropylethyl amine (1.2 mmol) in dichloromethane. After 1–16 hours, the mixture was diluted with dichloromethane and washed with 10% aqueous sodium bicarbonate. The combined organic extracts were dried over anhydrous sodium sulfate, filtered and concentrated.

Step B. To the residue was added an appropriately substituted arylboronic acid (1.2 mmol), potassium carbonate (2.5 mmol), tetrabutylammonium bromide (1 mmol), palladium(II)acetate (3% mole) and water/acetonitrile (1:1.2 mL). The mixture was heated at 70° C. for 1.5 hours, then ethyl acetate was added and the organic phase washed with water. The solution was filtered through a small plug of Celite and concentrated to dryness.

EXAMPLE 12

[3-Chloro-2'-methyl-(1,1'-biphenyl)-4-yl]-(5-methyl-5,11-dihydro-10H-dibenzo[b,e][1,4]diazepin-10-yl)-methanone HRMS [(+) ESI, m/z]: 439.15770 [M+H]$^+$. Calcd. for $C_{28}H_{24}ClN_2O$: 439.15716.

EXAMPLE 13

[3-Chloro-2'-methoxy-(1,1'-biphenyl)-4-yl]-(5-methyl-5,11-dihydro-10H-dibenzo[b,e][1,4]diazepin-10-yl)-methanone HRMS [(+) ESI, m/z]: 455.15195 [M+H]$^+$. Calcd. for $C_{28}H_{24}ClN_2O_2$: 455.15208.

EXAMPLE 14
[3-Chloro-3'-methoxy-(1,1'-biphenyl)-4-yl]-(5-methyl-5,11-dihydro-10H-dibenzo[b,e][1,4]diazepin-10-yl)-methanone HRMS [(+) ESI, m/z]: 455.15195 [M+H]$^+$. Calcd. for $C_{28}H_{24}ClN_2O_2$: 455.15208.

EXAMPLE 15
[2'-Methyl-(1,1'-biphenyl)-4-yl]-(5-methyl-5,11-dihydro-10H-dibenzo[b,e][1,4]diazepin-10-yl)-methanone HRMS [(+) ESI, m/z]: 405.19555 [M+H]$^+$. Calcd. for $C_{28}H_{25}N_2O$: 405.19614.

EXAMPLE 16
[2'-Methoxy-(1,1'-biphenyl)-4-yl]-(5-methyl-5,11-dihydro-10H-dibenzo[b,e][1,4]diazepin-10-yl)-methanone HRMS [(+) ESI, m/z]: 421.19021 [M+H]$^+$. Calcd. for $C_{28}H_{25}N_2O_2$: 421.19106.

EXAMPLE 17
[3'-Methoxy-(1,1'-biphenyl)-4-yl]-(5-methyl-5,11-dihydro-10H-dibenzo[b,e][1,4]diazepin-10-yl)-methanone HRMS [(+) ESI, m/z]: 421.19067 [M+H]$^+$. Calcd. for $C_{28}H_{25}N_2O_2$: 421.19106.

EXAMPLE 18
[3-Chloro-2'-methyl-(1,1'-biphenyl)-4-yl]-(11-methyl-5,11-dihydro-benzo[b]pyrido [2,3-e][1,4]diazepin-6-yl)-methanone HRMS [(+) ESI, m/z]: 440.15163 [M+H]$^+$. Calcd. for $C_{27}H_{23}ClN_3O$: 440.15241.

EXAMPLE 19
[3-Chloro-2'-methoxy-(1,1'-biphenyl)-4-yl]-(11-methyl-5,11-dihydro-benzo[b]pyrido [2,3-e][1,4]diazepin-6-yl)-methanone HRMS [(+) ESI, m/z]: 456.14731 [M+H]$^+$. Calcd. for $C_{27}H_{23}ClN_3O_2$: 456.14732.

EXAMPLE 20
[3-Chloro-3'-methoxy-(1,1'-biphenyl)-4-yl]-(11-methyl-5,11-dihydro-benzo[b]pyrido [2,3-e][1,4]diazepin-6-yl)-methanone HRMS [(+) ESI, m/z]: 456.14687 [M+H]$^+$. Calcd. for $C_{27}H_{23}ClN_3O_2$: 456.14732.

EXAMPLE 21
[2'-Methyl-(1,1'-biphenyl)-4-yl]-(11-methyl-5,11-dihydro-benzo[b]pyrido [2,3-e][1,4]diazepin-6-yl)-methanone HRMS [(+) ESI, m/z]: 406.19025 [M+H]$^+$. Calcd. for $C_{27}H_{24}N_3O$: 406.19139.

EXAMPLE 22
[2'-Methoxy-(1,1'-biphenyl)-4-yl]-(11-methyl-5,11-dihydro-benzo[b]pyrido [2,3-e][1,4]diazepin-6-yl)-methanone HRMS [(+) ESI, m/z]: 422.18706 [M+H]$^+$. Calcd. for $C_{27}H_{24}N_3O_2$: 422.18631.

EXAMPLE 23
[3'-Methoxy-(1,1'-biphenyl)-4-yl]-(11-methyl-5,11-dihydro-benzo[b]pyrido [2,3-e][1,4]diazepin-6-yl)-methanone HRMS [(+) ESI, m/z]: 422.18617 [M+H]$^+$. Calcd. for $C_{27}H_{24}N_3O_2$: 422.18631.

EXAMPLE 24
[3-Chloro-2'-methyl-(1,1'-biphenyl)-4-yl]-(10,11-dihydro-5H-pyrrolo[2,1-c][1,4]benzodiazepin-10-yl)-methanone HRMS [(+) ESI, m/z]: 413.14172 [M+H]$^+$. Calcd. for $C_{26}H22ClN_2O$: 413.14151.

EXAMPLE 25
[3-Chloro-2'-methoxy-(1,1'-biphenyl)-4-yl]-(10,11-dihydro-5H-pyrrolo[2,1-c][1,4]benzodiazepin-10-yl)-methanone HRMS [(+) ESI, m/z]: 429.13611 [M+H]$^+$. Calcd. for $C_{26}H_{22}ClN_2O_2$: 429.13643.

EXAMPLE 26
[3-Chloro-3'-methoxy-(1,1'-biphenyl)-4-yl]-(10,11-dihydro-5H-pyrrolo[2,1-c][1,4]benzodiazepin-10-yl)-methanone HRMS [(+) ESI, m/z]:,429.13622 [M+H]$^+$. Calcd. for $C_{26}H_{22}ClN_2O_2$: 429.13643.

EXAMPLE 27
[2'-Methyl-(1,1'-biphenyl)-4-yl]-(10,11-dihydro-5H-pyrrolo[2,1-c][1,4]benzodiazepin-10-yl)-methanone HRMS [(+) ESI, m/z]: 379.17963 [M+H]$^+$. Calcd. for $C_{26}H_{23}N_2O$: 379.18049.

EXAMPLE 28
[2'-Methoxy-(1,1'-biphenyl)-4-yl]-(10,11-dihydro-5H-pyrrolo[2,1-c][1,4]benzodiazepin-10-yl)-methanone HRMS [(+) ESI, m/z]: 395.17496 [M+H]$^+$. Calcd. for $C_{26}H_{23}N_2O_2$: 395.17541.

EXAMPLE 29
[3'-Methoxy-(1,1'-biphenyl)-4-yl]-(10,11-dihydro-5H-pyrrolo[2,1-c][1,4]benzodiazepin-10-yl)-methanone HRMS [(+) ESI, m/z]: 395.17529 [M+H]$^+$. Calcd. for $C_{26}H_{23}N_2O_2$: 395.17541.

What is claimed:

1. A method of treating disorders which are remedied or alleviated by vasopressin agonist activity in a mammal in need thereof, the method comprising administering to the mammal a pharmaceutically effective amount of a compound of Formula (I):

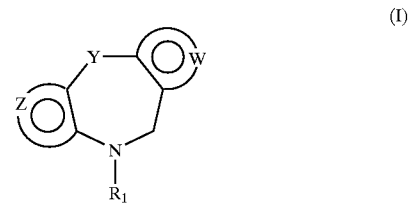

(I)

wherein:

Y is a moiety selected from $CH_2$;

represents a phenyl ring optionally substituted with one or two substituents selected, independently, from the group comprising hydrogen, ($C_1$–$C_6$) lower alkyl, halogen, cyano, $CF_3$, hydroxy, ($C_1$–$C_6$) lower alkoxy, ($C_1$–$C_6$) lower alkoxy carbonyl, carboxy, —$CONH_2$, —CONH[($C_1$–$C_6$) lower alkyl], —CON[($C_1$–$C_6$) lower alkyl]$_2$;

represents a 5-membered aromatic (unsaturated) heterocyclic ring having one nitrogen atom, optionally substituted by $(C_1-C_6)$ lower alkyl, $(C_1-C_6)$ lower alkoxy, or halogen;

$R_1$ is a moiety of the formula

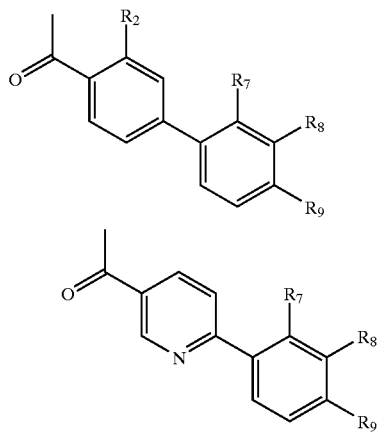

and $R_2$, $R_7$, $R_8$ and $R_9$ are, independently, selected from the group consisting of hydrogen, $(C_{1-C3})$ lower alkyl, $OCH_3$, halogen, $CF_3$, $-SCH_3$, $OCF_3$, $SCF_3$, or CN; or a pharmaceutically acceptable salt, or pro-drug form thereof.

2. The method of claim 1 wherein the disorder which is remedied or alleviated by vasopressin agonist activity is selected from the group of diabetes insipidus, nocturnal enuresis, nocturia, urinary incontinence, bleeding and coagulation disorders, or temporary delay of urination.

3. A compound selected from:
(2'-methoxy-[1,1'-biphenyl]-4-yl)-(5H, 11H-pyrrolo[2,1-c][1,4]benzodiazepin-10-yl)methanone;
(10,11-dihydro-5H-pyrrolo[2,1-c][1,4]benzodiazepin-10-yl)-(4'-methoxy-[1,1'-biphenyl]-4-yl)methanone;
(5H,11H-benzo[e]pyrrolo[1,2-a][1,4]diazepin-10-yl)(6-phenyl-pyridin-3-yl)methanone;
(5H-11H-benzo[e]pyrrolo[1,2-a][1,4]diazepin-10-yl)-(4'-methoxy-3-methyl-[1,1'-biphenyl]-4-yl)methanone;
[3-chloro-2'-methyl-(1,1'-biphenyl)-4-yl]-(10,11-dihydro-5H-pyrrolo[2,1-c][1,4]benzodiazepin-10-yl)methanone;
[3-chloro-2'-methoxy-(1,1'-biphenyl)-4-yl]-(10,11-dihydro-5H-pyrrolo[2,1-c][1,4]benzodiazepin-10-yl)methanone;
[3-chloro-3'-methoxy-(1,1'-biphenyl)-4-yl]-(10,11-dihydro-5H-pyrrolo[2,1-c][1,4]benzodiazepin-10-yl)methanone; and
[3'-methoxy-(1,1'-biphenyl)-4-yl]-(10,11-dihydro-5H-pyrrolo[2,1-c][1,4]benzodiazepin-10-yl)methanone;

or a pharmaceutically acceptable salt form thereof.

4. A method of treating disorders which are remedied or alleviated by vasopressin agonist activity in a mammal in need thereof, the method comprising administering to the mammal a pharmaceutically effective amount of a compound selected from:

(2'-methoxy-[1,1'-biphenyl]-4-yl)-(5H, 11H-pyrrolo[2,1-c][1,4]benzodiazepin-10-yl)methanone;
(10,11-dihydro-5H-pyrrolo[2,1-c][1,4]benzodiazepin-10-yl)-(3'-methyl-[1,1'-biphenyl]-4-yl)methanone;
(10,11-dihydro-5H-pyrrolo[2,1-c][1,4]benzodiazepin-10-yl)-(4'-methoxy-[1,1'-biphenyl]-4-yl)methanone;
(5H, 11H-benzo[e]pyrrolo[1,2-a][1,4]diazepin-10-yl)(6-phenyl-pyridin-3-yl)methanone;
(5H, 11H-benzo[e]pyrrolo[1,2-a][1,4]diazepin-10-yl)-(4'-methoxy-3-methyl-[1,1'-biphenyl]-4-yl)methanone;
[3-chloro-2'-methyl-(1,1'-biphenyl)-4-yl]-(10,11-dihydro-5H-pyrrolo[2,1-c][1,4]benzodiazepin-10-yl)methanone;
[3-chloro-2'-methoxy-(1,1'-biphenyl)-4-yl]-(10,11-dihydro-5H-pyrrolo[2,1-c][1,4]benzodiazepin-10-yl)methanone;
[3-chloro-3'-methoxy-(1,1'-biphenyl)-4-yl]-(10,11-dihydro-5H-pyrrolo[2,1-c][1,4]benzodiazepin-10-yl)methanone; and
[3'-methoxy-(1,1'-biphenyl)-4-yl]-(10,11-dihydro-5H-pyrrolo[2,1-c][1,4]benzodiazepin-10-yl)methanone;

or a pharmaceutically acceptable salt form thereof.

5. The method of claim 4 wherein the disorder which is remedied or alleviated by vasopressin agonist activity is selected from the group of diabetes insipidus, nocturnal enuresis, nocturia, urinary incontinence, bleeding and coagulation disorders, or temporary delay of urination.

6. A pharmaceutical composition comprising a pharmaceutically effective amount of a compound of claim 3 and a pharmaceutically acceptable carrier.

\* \* \* \* \*

UNITED STATES PATENT AND TRADEMARK OFFICE
CERTIFICATE OF CORRECTION

PATENT NO.     : 6,903,091 B2  Page 1 of 1
DATED          : June 7, 2005
INVENTOR(S)    : A. Failli et al.

It is certified that error appears in the above-identified patent and that said Letters Patent is hereby corrected as shown below:

Column 17,
Lines 2-55, replace Scheme VII with the following:

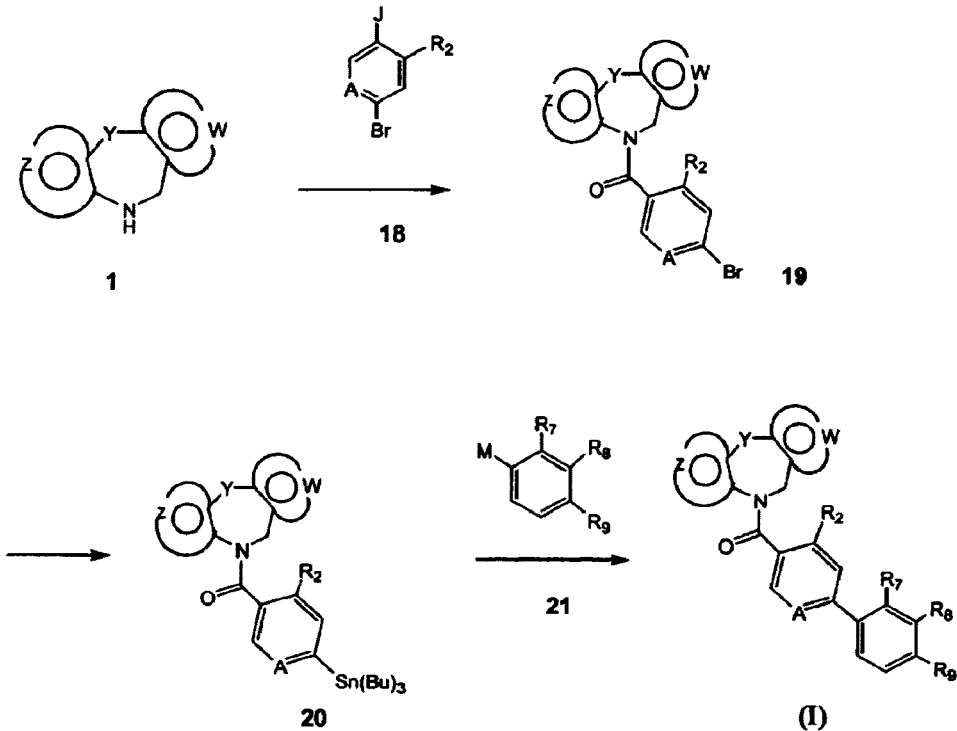

Signed and Sealed this

Seventh Day of February, 2006

JON W. DUDAS
*Director of the United States Patent and Trademark Office*